(12) United States Patent
Adams et al.

(10) Patent No.: US 8,865,167 B2
(45) Date of Patent: *Oct. 21, 2014

(54) NEUTRALISING ANTIBODY MOLECULES HAVING SPECIFICITY FOR HUMAN IL-17

(71) Applicant: UCB Pharma S.A., Brussels (BE)

(72) Inventors: Ralph Adams, Slough (GB); Andrew George Popplewell, Slough (GB); Stephen Edward Rapecki, Slough (GB); Simon Peter Tickle, Slough (GB)

(73) Assignee: UCB Pharma, S.A., Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/709,055

(22) Filed: Dec. 9, 2012

(65) Prior Publication Data

US 2013/0245229 A1 Sep. 19, 2013

Related U.S. Application Data

(63) Continuation of application No. 11/791,109, filed as application No. PCT/GB2005/004392 on Nov. 16, 2005, now Pat. No. 8,231,875.

(30) Foreign Application Priority Data

Nov. 19, 2004 (GB) .................................. 0425569.1

(51) Int. Cl.

| A61K 39/395 | (2006.01) |
|---|---|
| A61K 39/00 | (2006.01) |
| A61K 47/48 | (2006.01) |
| C07K 16/24 | (2006.01) |
| C07K 16/46 | (2006.01) |

(52) U.S. Cl.
CPC ......... *C07K 16/464* (2013.01); *A61K 2039/505* (2013.01); *C07K 2317/24* (2013.01); *C07K 2317/55* (2013.01); *A61K 47/48215* (2013.01); *C07K 2317/76* (2013.01); *C07K 2317/565* (2013.01); *C07K 16/244* (2013.01); *C07K 2317/92* (2013.01)
USPC .................. 424/133.1; 530/387.3; 530/391.1; 530/351

(58) Field of Classification Search
None
See application file for complete search history.

(56) References Cited

U.S. PATENT DOCUMENTS

| 6,274,711 B1 * | 8/2001 | Golstein et al. ............. 530/389.2 |
|---|---|---|
| 8,231,875 B2 * | 7/2012 | Adams et al. ............. 424/133.1 |
| 2007/0009959 A1 | 1/2007 | Lawson et al. | |
| 2008/0181888 A1 | 7/2008 | Ambrose et al. | |

FOREIGN PATENT DOCUMENTS

| WO | 00/69463 | 11/2000 |
|---|---|---|
| WO | 2004/106377 | 12/2004 |
| WO | 2005/010044 | 2/2005 |
| WO | 2005/051422 | 6/2005 |
| WO | 2006/013107 | 2/2006 |
| WO | 2006/088833 | 8/2006 |

OTHER PUBLICATIONS

Boder, et al., "Direct evolution of antibody fragments with monvalent femtomolar antigen-binding affinity", Proceedings of the National Academy of Sciences of USA, vol. 97, No. 20, Sep. 26, 2000, pp. 10701-10705.
Burchill, et al., "Inhibition of interleukin-17 prevents the development of arthritis in vaccinated mice challenged with *Borrelia burgdorferi*", Infection and Immunity, vol. 71, No. 6, Jun. 2003, pp. 3437-3442.
Doo, et al., "CD4+ T cells regulate surgical and postinfection adhesion formation", The Journal of Experimental Medicine, Jun. 3, 2002, vol. 195, No. 11, Jun. 3, 2002, pp. 1471-1478.
Davies, et al., "Affinity improvement of single antibody VH domains: residues in all three hypervariable regions affect antigen binding", Immunotechnology, vol. 2, No. 3, Sep. 1996, pp. 169-179.
Dumont, F. J., "IL-17 cytokine/receptor families: Emerging targets for the modulation of inflammatory responses", Expert Opinion of Therapeutic Patents, Ashley Publications, GB vol. 13, No. 3, Mar. 1, 2003, pp. 287-3030.
Hellings, et al., "Interleukin-17 orchestrates the granulocyte influx into airways after allergen inhalation in a mouse model of allergic asthma", American Journal of Respiratory Cell and Molecular biology, vol. 28, No. 1, Jan. 2003, pp. 42-50.
Holt, et al., "Domain antibodies: proteins for therapy", Trends in Biotechnology, vol. 21, No. 11, Nov. 2003, p. 482-490.
Numasaki, et al., "Interleukin-17 promotes angiogenesis and tumor growth", Blood, vol. 101, No. 7, Apr. 1, 2003, pp. 2620-2627.
Pascalis, et al., "Grafting of 'abbreviated' complementary-determining regions containing specificity determining residues essential for ligand contact to engineer a less immunogenic hmanized monoclonal antibody", J. Immunol., 2002, 169:3076-3084.
Thompson, et al., "Affinity maturation of a high-affinity human monoclonal antibody against the third hypervariable loop of human immunodeficiency virus: use of phage display to improve affiinity and broaden strain reactivity", Journal of Molecular Biology, vol. 256, No. 1, Feb. 16, 1996, pp. 77-88.
Paul, "Fv Structure and Diversity in Three Dimensions", Fundamental Immunology, 3rd Edition, 1993, pp. 292-295.
Kotake, et al., "IL-17 in synovial fluids from patients with rheumatoid arthritis in a potent stimulator of osteoclastogenesis", The Journal of Clinical Investigation, 103:1345-1352 (1999).
R & D Systems: "Monoclonal Anti-Human IL-17 Antibody", Announcement R&D Systems, Jan. 11, 2004, pp. 1-2.

(Continued)

*Primary Examiner* — Dong Jiang
(74) *Attorney, Agent, or Firm* — McDonnell Boehnen Hulbert & Berghoff LLP

(57) ABSTRACT

The invention relates to an antibody molecule having specificity for antigenic determinants of IL-17, therapeutic uses of the antibody molecule and methods for producing said antibody molecule.

7 Claims, 17 Drawing Sheets

(56) References Cited

OTHER PUBLICATIONS

Figure 6:
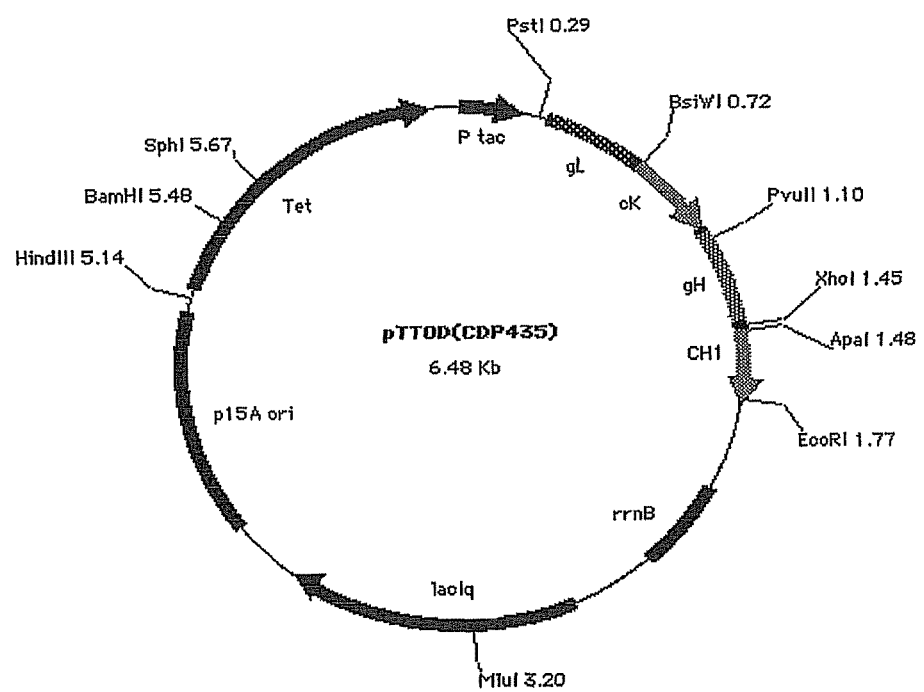

Chabaud, M., et al., "Contribution of Interleukin 17 to Synovium Matrix Destruction in Rheumatoid Arthritis", Cytokine Academic Press Ltd., vol. 12, No. 7, Jul. 2000, pp. 1092-1099.

Vandamme, et al., Construction and characterization of a recombinant murine monoclonal antibody directed against human fibrin fragment-D dimer, J. Biochem., 192:767-775 (1990).

International Search Report, PCT/GB2005/004392, dated Feb. 14, 2006.

* cited by examiner

Figure 1

(a)

```
            10               20               30               40
   ATG GCT GTC CTA GGG CTG CTC TTC TGC CTG GTG ACT TTC CCA
   TAC CGA CAG GAT CCC GAC GAG AAG ACG GAC CAC TGA AAG GGT
    M   A   V   L   G   L   L   F   C   L   V   T   F   P>

50               60               70               80
   AGC TGT GTC CTG TCC CAG GTG CAG CTG AAG GAG TCA GGA CCT
   TCG ACA CAG GAC AGG GTC CAC GTC GAC TTC CTC AGT CCT GGA
    S   C   V   L   S   Q   V   Q   L   K   E   S   G   P>

90              100              110              120
   GGC CTG GTG GCG CCC TCA CAG AGC CTG TCC ATC ACA TGC ACC
   CCG GAC CAC CGC GGG AGT GTC TCG GAC AGG TAG TGT ACG TGG
    G   L   V   A   P   S   Q   S   L   S   I   T   C   T>

130              140              150              160
   GTC TCA GGG TTC TCA TTA ACT ACC TAT GGT GTA CAC TGG ATT
   CAG AGT CCC AAG AGT AAT TGA TGG ATA CCA CAT GTG ACC TAA
    V   S   G   F   S   L   T   T   Y   G   V   H   W   I>

170              180              190              200              210
   CGC CAG CCT CCA GGA AAG GGT CTG GAG TGG CTG GTA GTG ATT
   GCG GTC GGA GGT CCT TTC CCA GAC CTC ACC GAC CAT CAC TAA
    R   Q   P   P   G   K   G   L   E   W   L   V   V   I>

220              230              240              250
   TGG AGT GAT GGA TAC ACA ACC TAT AAT TCA GCT CTC AAA TCC
   ACC TCA CTA CCT ATG TGT TGG ATA TTA AGT CGA GAG TTT AGG
    W   S   D   G   Y   T   T   Y   N   S   A   L   K   S>

260              270              280              290
   AGA CTG AGC ATC ACC AAG GAC AAC TCC AAG AGC CAA GTT TTC
   TCT GAC TCG TAG TGG TTC CTG TTG AGG TTC TCG GTT CAA AAG
    R   L   S   I   T   K   D   N   S   K   S   Q   V   F>

300              310              320              330
   TTA AAA ATG AAC AGT CTC CAA ACT GAT GAC ACA GCC ATG TAC
   AAT TTT TAC TTG TCA GAG GTT TGA CTA CTG TGT CGG TAC ATG
    L   K   M   N   S   L   Q   T   D   D   T   A   M   Y>

340              350              360              370
   TAC TGT GCC AGA AAT GAT GGT GAC TAC TTC TAT TCT ATG GAC
   ATG ACA CGG TCT TTA CTA CCA CTG ATG AAG ATA AGA TAC CTG
    Y   C   A   R   N   D   G   D   Y   F   Y   S   M   D>

380              390              400              410
   TAC TGG GGT CAA GGA ACC TCA GTC ACC GTC TCC TCA
   ATG ACC CCA GTT CCT TGG AGT CAG TGG CAG AGG AGT
    Y   W   G   Q   G   T   S   V   T   V   S   S>
```

Figure 1 (Cont'd)

(b)

```
              10            20            30            40
ATG AAG TTG CCT GTT AGG CTG TTG GTG CTG ATG TTC TGG ATT
TAC TTC AAC GGA CAA TCC GAC AAC CAC GAC TAC AAG ACC TAA
 M   K   L   P   V   R   L   L   V   L   M   F   W   I>

50            60            70            80
CCT GCT TCC AGC AGT GAT GTT GTG ATG ACC CAA ACT CCA CTC
GGA CGA AGG TCG TCA CTA CAA CAC TAC TGG GTT TGA GGT GAG
 P   A   S   S   S   D   V   V   M   T   Q   T   P   L>

90           100           110           120
TCC CTG CCT GTC AGT CTT GGA GAT CAA GCC TCC TTC TCT TGC
AGG GAC GGA CAG TCA GAA CCT CTA GTT CGG AGG AAG AGA ACG
 S   L   P   V   S   L   G   D   Q   A   S   F   S   C>

130           140           150           160
AGA TCT AGT CAG AGC CTT GTA CAC AGT AAT GGA AAC ACC TAT
TCT AGA TCA GTC TCG GAA CAT GTG TCA TTA CCT TTG TGG ATA
 R   S   S   Q   S   L   V   H   S   N   G   N   T   Y>

170           180           190           200           210
TTA CAT TGG TAC CTG CAG AAG CCA GGC CAG TCT CCA AAG CTC
AAT GTA ACC ATG GAC GTC TTC GGT CCG GTC AGA GGT TTC GAG
 L   H   W   Y   L   Q   K   P   G   Q   S   P   K   L>

220           230           240           250
CTG ATC TAC AAA GTT TCC AAC CGA TTT TCT GGG GTC CCA GAC
GAC TAG ATG TTT CAA AGG TTG GCT AAA AGA CCC CAG GGT CTG
 L   I   Y   K   V   S   N   R   F   S   G   V   P   D>

260           270           280           290
AGG TTC AGT GGC AGT GGG TCA GGG ACA GAT TTC ACA CTC AAG
TCC AAG TCA CCG TCA CCC AGT CCC TGT CTA AAG TGT GAG TTC
 R   F   S   G   S   G   S   G   T   D   F   T   L   K>

300           310           320           330
ATC AGC AGA GTG GAG GCT GAG GAT CTG GGA GTT TAT TTC TGC
TAG TCG TCT CAC CTC CGA CTC CTA GAC CCT CAA ATA AAG ACG
 I   S   R   V   E   A   E   D   L   G   V   Y   F   C>

340           350           360           370
TCT CAA AGT ACA CAT GTT CCG ACG TTC GGT GGA GGC ACC AAG
AGA GTT TCA TGT GTA CAA GGC TGC AAG CCA CCT CCG TGG TTC
 S   Q   S   T   H   V   P   T   F   G   G   G   T   K>

380           390
CTG GAA ATC AAA CGT ACG
GAC CTT TAG TTT GCA TGC
 L   E   I   K   R   T>
```

Figure 2

(a)

```
           1       5        10        15        20        25        30        35        40        45        50  a  55        60        65        70        75        80 abc 85        90        95      100abc  105       110
F4.100 VH  QVQLKESGPGLIVAPSQSLSITCTVSGFSLTTYGVHWLRQPPGKGLEWLVVIW SDGYTTYNSALKSRLSITKDNSKSQVFLKMNSLQTDDTAMYYCARNDGDYFYSMDYNGQGTSVTVSS
3.33       QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCAR                    WGQGTLVTVSS
                *
gH11       EVQLVESGGGVVQPGGSLRLSCAVSGFSLTTYGVHWVRQAPGKGLEWVAVIW SDGYTTYNSALKSRFTISRDNSKNTVYLQMNSLRAEDTAVYYCARNDGDYFYSMDYWGQGTLVTVSS
                *
```

(b)

```
           1       5        10        15        20        25  abcde 30        35        40        45        50        55        60        65        70        75        80        85        90        95       100       105
F4.100 VK  DVVMTQTPLSLPVSLGDQASFSCRSSQSLVHSNGNTYLHWYLQKPGQSPKLLIYKVSNRFSGVPDRFSGSGSGTDFTLKISRVEAEDLGVYFCSQSTHVP TFGGGTKLEIK
O12        DIQMTQSPSSLSASVGDRVTITCRASQ                 SISSYLNWYQQKPGKAPKLLIYAASSLQSGVPSRFSGSGSGTDFTLTISSLQPEDFATYYCQQSYSTP   FGQGTKVEIK
gL3        DVQMTQSPSSLSASVGDRVTITCRSSQSLVHSNGNTYLHWYQQKPGKAPKLLIYKVSNRFSGVPSRFSGSGSGTDFTLTISSLQPEDFATYYCSQSTHVP TFGQGTKVEIK
```

Figure 3

(a)

```
            10              20              30              40              50
ATG AAG AAG ACT GCT ATA GCA ATT GCA GTG GCG CTA GCT GGT TTC GCC ACC GTG
TAC TTC TTC TGA CGA TAT CGT TAA CGT CAC CGC GAT CGA CCA AAG CGG TGG CAC
 M   K   K   T   A   I   A   I   A   V   A   L   A   G   F   A   T   V>

60              70              80              90             100
GCG CAA GCT GAG GTT CAG CTG GTC GAG TCT GGA GGC GGG GTT GTC CAG CCT GGA
CGC GTT CGA CTC CAA GTC GAC CAG CTC AGA CCT CCG CCC CAA CAG GTC GGA CCT
 A   Q   A   E   V   Q   L   V   E   S   G   G   G   V   V   Q   P   G>

110             120             130             140             150             160
GGG AGC CTG CGT CTC TCT TGT GCA GTT AGC GGC TTC TCA TTA ACT ACC TAT GGT
CCC TCG GAC GCA GAG AGA ACA CGT CAA TCG CCG AAG AGT AAT TGA TGG ATA CCA
 G   S   L   R   L   S   C   A   V   S   G   F   S   L   T   T   Y   G>

170             180             190             200             210
GTA CAC TGG GTG CGG CAG GCA CCT GGG AAG GGC CTG GAG TGG GTG GCC GTG ATT
CAT GTG ACC CAC GCC GTC CGT GGA CCC TTC CCG GAC CTC ACC CAC CGG CAC TAA
 V   H   W   V   R   Q   A   P   G   K   G   L   E   W   V   A   V   I>

220             230             240             250             260             270
TGG AGT GAT GGA TAC ACA ACC TAT AAT TCA GCT CTC AAA TCC CGT TTC ACC ATT
ACC TCA CTA CCT ATG TGT TGG ATA TTA AGT CGA GAG TTT AGG GCA AAG TGG TAA
 W   S   D   G   Y   T   T   Y   N   S   A   L   K   S   R   F   T   I>

280             290             300             310             320
TCC CGC GAC AAT TCT AAG AAC ACC GTT TAC CTC CAG ATG AAC TCT CTC CGC GCA
AGG GCG CTG TTA AGA TTC TTG TGG CAA ATG GAG GTC TAC TTG AGA GAG GCG CGT
 S   R   D   N   S   K   N   T   V   Y   L   Q   M   N   S   L   R   A>

330             340             350             360             370
GAG GAC ACA GCA GTC TAT TAC TGT GCA CGG AAT GAT GGT GAC TAC TTC TAT TCT
CTC CTG TGT CGT CAG ATA ATG ACA CGT GCC TTA CTA CCA CTG ATG AAG ATA AGA
 E   D   T   A   V   Y   Y   C   A   R   N   D   G   D   Y   F   Y   S>

380             390             400             410             420
ATG GAC TAC TGG GGA CAG GGG ACC CTT GTG ACA GTC TCG AGT
TAC CTG ATG ACC CCT GTC CCC TGG GAA CAC TGT CAG AGC TCA
 M   D   Y   W   G   Q   G   T   L   V   T   V   S   S>
```

(b)

```
            10              20              30              40              50
ATG AAA AAG ACA GCT ATC GCA ATT GCA GTG GCC TTG GCT GGT TTC GCT ACC GTA
TAC TTT TTC TGT CGA TAG CGT TAA CGT CAC CGG AAC CGA CCA AAG CGA TGG CAT
 M   K   K   T   A   I   A   I   A   V   A   L   A   G   F   A   T   V>

60              70              80              90             100
GCG CAA GCT GAT GTG CAG ATG ACC CAG AGT CCA AGC AGT CTC TCC GCC AGC GTA
CGC GTT CGA CTA CAC GTC TAC TGG GTC TCA GGT TCG TCA GAG AGG CGG TCG CAT
 A   Q   A   D   V   Q   M   T   Q   S   P   S   S   L   S   A   S   V>

110             120             130             140             150             160
GGC GAT CGT GTG ACT ATT ACC TGT AGA TCT AGT CAG AGC CTT GTA CAC AGT AAT
CCG CTA GCA CAC TGA TAA TGG ACA TCT AGA TCA GTC TCG GAA CAT GTG TCA TTA
 G   D   R   V   T   I   T   C   R   S   S   Q   S   L   V   H   S   N>

170             180             190             200             210
GGA AAC ACC TAT TTA CAT TGG TAT CAG CAA AAA CCG GGC AAA GCC CCG AAG CTG
CCT TTG TGG ATA AAT GTA ACC ATA GTC GTT TTT GGC CCG TTT CGG GGC TTC GAC
 G   N   T   Y   L   H   W   Y   Q   Q   K   P   G   K   A   P   K   L>
```

Figure 3 (Cont'd)

```
        220         230         240         250         260         270
CTC ATC TAT AAA GTT TCC AAC CGA TTT TCT GGT GTG CCA TCT CGT TTC AGT GGC
GAG TAG ATA TTT CAA AGG TTG GCT AAA AGA CCA CAC GGT AGA GCA AAG TCA CCG
 L   I   Y   K   V   S   N   R   F   S   G   V   P   S   R   F   S   G>

280         290         300         310         320
AGT GGC AGC GGT ACC GAC TTT ACC CTC ACA ATT TCG TCT CTC CAG CCG GAA GAT
TCA CCG TCG CCA TGG CTG AAA TGG GAG TGT TAA AGC AGA GAG GTC GGC CTT CTA
 S   G   S   G   T   D   F   T   L   T   I   S   S   L   Q   P   E   D>

330         340         350         360         370
TTC GCC ACT TAC TAT TGT TCT CAA AGT ACA CAT GTT CCG ACG TTC GGT CAG GGC
AAG CGG TGA ATG ATA ACA AGA GTT TCA TGT GTA CAA GGC TGC AAG CCA GTC CCG
 F   A   T   Y   Y   C   S   Q   S   T   H   V   P   T   F   G   Q   G>

380         390
ACT AAA GTA GAA ATC AAA CGT
TGA TTT CAT CTT TAG TTT GCA
 T   K   V   E   I   K   R>
```

Figure 4

(a)

DVQMTQSPSSLSASVGDRVTITCRSSQSLVHSNGNTYLHWYQQKPGKAPKLLIYKVSNRFSGVP
SRFSGSGSGTDFTLTISSLQPEDFATYYCSQSTHVPTFGQGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC*

(b)

EVQLVESGGGVVQPGGSLRLSCAVSGFSLTTYGVHWVRQAPGKGLEWVAVIWSDGYTTYNSALK
SRFTISRDNSKNTVYLQMNSLRAEDTAVYYCARNDGDYFYSMDYWGQGTLVTVSSASTKGPSVF
PLAPSSKSTSGGTAALGCLVKDYFPEPVTVSWNSGALTSGVHTFPAVLQSSGLYSLSSVVTVPS
SSLGTQTYICNVNHKPSNTKVDKKVEPKSC*

Figure 5

```
              10             20             30             40             50             60
ATG AAA AAG ACA GCT ATC GCA ATT GCA GTG GCC TTG GCT GGT TTC GCT ACC GTA GCG CAA
TAC TTT TTC TGT CGA TAG CGT TAA CGT CAC CGG AAC CGA CCA AAG CGA TGG CAT CGC GTT
 M   K   K   T   A   I   A   I   A   V   A   L   G   F   A   T   V   A   Q>

70             80             90            100            110            120
GCT GAT GTG CAG ATG ACC CAG AGT CCA AGC AGT CTC TCC GCC AGC GTA GGC GAT CGT GTG
CGA CTA CAC GTC TAC TGG GTC TCA GGT TCG TCA GAG AGG CGG TCG CAT CCG CTA GCA CAC
 A   D   V   Q   M   T   Q   S   P   S   S   L   S   A   S   V   G   D   R   V>

130            140            150            160            170            180
ACT ATT ACC TGT AGA TCT AGT CAG AGC CTT GTA CAC AGT AAT GGA AAC ACC TAT TTA CAT
TGA TAA TGG ACA TCT AGA TCA GTC TCG GAA CAT GTG TCA TTA CCT TTG TGG ATA AAT GTA
 T   I   T   C   R   S   S   Q   S   L   V   H   S   N   G   N   T   Y   L   H>

190            200            210            220            230            240
TGG TAT CAG CAA AAA CCG GGC AAA GCC CCG AAG CTG CTC ATC TAT AAA GTT TCC AAC CGA
ACC ATA GTC GTT TTT GGC CCG TTT CGG GGC TTC GAC GAG TAG ATA TTT CAA AGG TTG GCT
 W   Y   Q   Q   K   P   G   K   A   P   K   L   L   I   Y   K   V   S   N   R>

250            260            270            280            290            300
TTT TCT GGT GTG CCA TCT CGT TTC AGT GGC AGT GGC AGC GGT ACC GAC TTT ACC CTC ACA
AAA AGA CCA CAC GGT AGA GCA AAG TCA CCG TCA CCG TCG CCA TGG CTG AAA TGG GAG TGT
 F   S   G   V   P   S   R   F   S   G   S   G   S   G   T   D   F   T   L   T>

310            320            330            340            350            360
ATT TCG TCT CTC CAG CCG GAA GAT TTC GCC ACT TAC TAT TGT TCT CAA AGT ACA CAT GTT
TAA AGC AGA GAG GTC GGC CTT CTA AAG CGG TGA ATG ATA ACA AGA GTT TCA TGT GTA CAA
 I   S   S   L   Q   P   E   D   F   A   T   Y   Y   C   S   Q   S   T   H   V>

370            380            390            400            410            420
CCG ACG TTC GGT CAG GGC ACT AAA GTA GAA ATC AAA CGT ACG GTA GCG GCC CCA TCT GTC
GGC TGC AAG CCA GTC CCG TGA TTT CAT CTT TAG TTT GCA TGC CAT CGC CGG GGT AGA CAG
 P   T   F   G   Q   G   T   K   V   E   I   K   R   T   V   A   A   P   S   V>

430            440            450            460            470            480
TTC ATC TTC CCG CCA TCT GAT GAG CAG TTG AAA TCT GGA ACT GCC TCT GTT GTG TGC CTG
AAG TAG AAG GGC GGT AGA CTA CTC GTC AAC TTT AGA CCT TGA CGG AGA CAA CAC ACG GAC
 F   I   F   P   P   S   D   E   Q   L   K   S   G   T   A   S   V   V   C   L>

490            500            510            520            530            540
CTG AAT AAC TTC TAT CCC AGA GAG GCC AAA GTA CAG TGG AAG GTG GAT AAC GCC CTC CAA
GAC TTA TTG AAG ATA GGG TCT CTC CGG TTT CAT GTC ACC TTC CAC CTA TTG CGG GAG GTT
 L   N   N   F   Y   P   R   E   A   K   V   Q   W   K   V   D   N   A   L   Q>

550            560            570            580            590            600
TCG GGT AAC TCC CAG GAG AGT GTC ACA GAG CAG GAC AGC AAG GAC AGC ACC TAC AGC CTC
AGC CCA TTG AGG GTC CTC TCA CAG TGT CTC GTC CTG TCG TTC CTG TCG TGG ATG TCG GAG
 S   G   N   S   Q   E   S   V   T   E   Q   D   S   K   D   S   T   Y   S   L>

610            620            630            640            650            660
AGC AGC ACC CTG ACG CTG AGC AAA GCA GAC TAC GAG AAA CAC AAA GTC TAC GCC TGC GAA
TCG TCG TGG GAC TGC GAC TCG TTT CGT CTG ATG CTC TTT GTG TTT CAG ATG CGG ACG CTT
 S   S   T   L   T   L   S   K   A   D   Y   E   K   H   K   V   Y   A   C   E>

670            680            690            700            710            720
GTC ACC CAT CAG GGC CTG AGC TCA CCA GTA ACA AAA AGT TTT AAT AGA GGG GAG TGT TAA
CAG TGG GTA GTC CCG GAC TCG AGT GGT CAT TGT TTT TCA AAA TTA TCT CCC CTC ACA ATT
 V   T   H   Q   G   L   S   S   P   V   T   K   S   F   N   R   G   E   C   *>

730            740            750            760            770            780
A ATG AAG AAG ACT GCT ATA GCA ATT GCA GTG GCG CTA GCT GGT TTC GCC ACC GTG GCG CAA
T TAC TTC TTC TGA CGA TAT CGT TAA CGT CAC CGC GAT CGA CCA AAG CGG TGG CAC CGC GTT
    M   K   K   T   A   I   A   I   A   V   A   L   A   G   F   A   T   V   A   Q>

790            800            810            820            830            840
  GCT GAG GTT CAG CTG GTC GAG TCT GGA GGC GGG GTT GTC CAG CCT GGA GGG AGC CTG CGT
```

Figure 5 (Cont'd)

```
CGA CTC CAA GTC GAC CAG CTC AGA CCT CCG CCC CAA CAG GTC GGA CCT CCC TCG GAC GCA
 A   E   V   Q   L   V   E   S   G   G   G   V   V   Q   P   G   G   S   L   R>

850         860         870         880         890         900
CTC TCT TGT GCA GTT AGC GGC TTC TCA TTA ACT ACC TAT GGT GTA CAC TGG GTG CGG CAG
GAG AGA ACA CGT CAA TCG CCG AAG AGT AAT TGA TGG ATA CCA CAT GTG ACC CAC GCC GTC
 L   S   C   A   V   S   G   F   S   L   T   T   Y   G   V   H   W   V   R   Q>

910         920         930         940         950         960
GCA CCT GGG AAG GGC CTG GAG TGG GTG GCC GTG ATT TGG AGT GAT GGA TAC ACA ACC TAT
CGT GGA CCC TTC CCG GAC CTC ACC CAC CGG CAC TAA ACC TCA CTA CCT ATG TGT TGG ATA
 A   P   G   K   G   L   E   W   V   A   V   I   W   S   D   G   Y   T   T   Y>

970         980         990         1000        1010        1020
AAT TCA GCT CTC AAA TCC CGT TTC ACC ATT TCC CGC GAC AAT TCT AAG AAC ACC GTT TAC
TTA AGT CGA GAG TTT AGG GCA AAG TGG TAA AGG GCG CTG TTA AGA TTC TTG TGG CAA ATG
 N   S   A   L   K   S   R   F   T   I   S   R   D   N   S   K   N   T   V   Y>

1030        1040        1050        1060        1070        1080
CTC CAG ATG AAC TCT CTC CGC GCA GAG GAC ACA GCA GTC TAT TAC TGT GCA CGG AAT GAT
GAG GTC TAC TTG AGA GAG GCG CGT CTC CTG TGT CGT CAG ATA ATG ACA CGT GCC TTA CTA
 L   Q   M   N   S   L   R   A   E   D   T   A   V   Y   Y   C   A   R   N   D>

1090        1100        1110        1120        1130        1140
GGT GAC TAC TTC TAT TCT ATG GAC TAC TGG GGA CAG GGG ACC CTT GTG ACA GTC TCG AGT
CCA CTG ATG AAG ATA AGA TAC CTG ATG ACC CCT GTC CCC TGG GAA CAC TGT CAG AGC TCA
 G   D   Y   F   Y   S   M   D   Y   W   G   Q   G   T   L   V   T   V   S   S>

1150        1160        1170        1180        1190        1200
GCT TCT ACA AAG GGC CCA TCG GTC TTC CCC CTG GCA CCC TCC TCC AAG AGC ACC TCT GGG
CGA AGA TGT TTC CCG GGT AGC CAG AAG GGG GAC CGT GGG AGG AGG TTC TCG TGG AGA CCC
 A   S   T   K   G   P   S   V   F   P   L   A   P   S   S   K   S   T   S   G>

1210        1220        1230        1240        1250        1260
GGC ACA GCG GCC CTG GGC TGC CTG GTC AAG GAC TAC TTC CCC GAA CCG GTG ACG GTG TCG
CCG TGT CGC CGG GAC CCG ACG GAC CAG TTC CTG ATG AAG GGG CTT GGC CAC TGC CAC AGC
 G   T   A   A   L   G   C   L   V   K   D   Y   F   P   E   P   V   T   V   S>

1270        1280        1290        1300        1310        1320
TGG AAC TCA GGC GCC CTG ACC AGC GGC GTG CAC ACC TTC CCG GCT GTC CTA CAG TCC TCA
ACC TTG AGT CCG CGG GAC TGG TCG CCG CAC GTG TGG AAG GGC CGA CAG GAT GTC AGG AGT
 W   N   S   G   A   L   T   S   G   V   H   T   F   P   A   V   L   Q   S   S>

1330        1340        1350        1360        1370        1380
GGA CTC TAC TCC CTC AGC AGC GTG GTG ACC GTG CCC TCC AGC AGC TTG GGC ACC CAG ACC
CCT GAG ATG AGG GAG TCG TCG CAC CAC TGG CAC GGG AGG TCG TCG AAC CCG TGG GTC TGG
 G   L   Y   S   L   S   S   V   V   T   V   P   S   S   L   G   T   Q   T>

1390        1400        1410        1420        1430        1440
TAC ATC TGC AAC GTG AAT CAC AAG CCC AGC AAC ACC AAG GTC GAC AAG AAA GTT GAG CCC
ATG TAG ACG TTG CAC TTA GTG TTC GGG TCG TTG TGG TTC CAG CTG TTC TTT CAA CTC GGG
 Y   I   C   N   V   N   H   K   P   S   N   T   K   V   D   K   K   V   E   P>

1450
AAA TCT TGT TAA TGA
TTT AGA ACA ATT ACT
 K   S   C   *   *>
```

Pharmacokinetic data

AUC (0-∞) (%dose*h)    2469 ± 4.40 t1/2 absorption (h)    27.5 ± 15.9 t1/2β (h)              30.6 ± 13.0

Cmax (%dose)           21.6 ± 6.30 n is between 400 and 520

NEUTRALISING ANTIBODY MOLECULES HAVING SPECIFICITY FOR HUMAN IL-17

This application is a continuation of U.S. application Ser. No. 13/218,857, filed Aug. 26, 2011, now U.S. Pat. No. 8,329,431, which is a divisional of U.S. patent application Ser. No. 11/791,109 filed May 17, 2007, now U.S. Pat. No. 8,231,875, which is a U.S. national phase of International Application No. PCT/GB2005/004392, filed Nov. 16, 2005, the disclosures of which are incorporated herein by reference in their entirety.

The present invention relates to an antibody molecule having specificity for antigenic determinants of IL-17. The present invention also relates to the therapeutic uses of the antibody molecule and methods for producing the antibody molecule.

Interleukin 17 (IL-17), also known as CTLA-8 or IL-17A, is a pro-inflammatory cytokine which stimulates the secretion of a wide range of other cytokines from various non-immune cells. IL-17 is capable of inducing the secretion of IL-6, IL-8, PGE2, MCP-1 and G-CSF by adherent cells like fibroblasts, keratinocytes, epithelial and endothelial cells and is also able to induce ICAM-1 surface expression, proliferation of T cells, and growth and differentiation of CD34+ human progenitors into neutrophils when cocultured in the presence of irradiated fibroblasts (Fossiez et al., 1998, Int. Rev. Immunol. 16, 541-551). IL-17 is predominantly produced by activated memory T cells and acts by binding to a ubiquitously distributed cell surface receptor (IL-17R) (Yao et al., 1997, Cytokine, 9, 794-800). A number of homologues of IL-17 have been identified which have both similar and distinct roles in regulating inflammatory responses. For a review of IL-17 cytokine/receptor families see Dumont, 2003, Expert Opin. Ther. Patents, 13, 287-303.

IL-17 may contribute to a number of diseases mediated by abnormal immune responses, such as rheumatoid arthritis and air-way inflammation, as well as organ transplant rejection and antitumour immunity Inhibitors of IL-17 activity are well known in the art for example a murine IL-17R:human Fc fusion protein, a murine soluble IL-17R and an anti-IL-17 monoclonal antibody have been used to demonstrate the role of IL-17 in various models of rheumatoid arthritis (Lubberts et al., J. Immunol. 2001, 167, 1004-1013; Chabaud et al., Arthritis Res. 2001, 3, 168-177). In addition, neutralising polyclonal antibodies have been used to reduce peritoneal adhesion formation (Chung et al., 2002, J. Exp. Med., 195, 1471-1478). To date no anti-human IL-17 antibodies have been developed for use in therapy and hence there is a need for a high affinity, anti-IL-17 antibody suitable for treating patients.

We have now identified a high affinity neutralising anti-IL-17 antibody that is particularly efficacious in vivo, for example in the in vivo inflammation models described herein.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus 'CDR-H1', as used herein, comprises residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

As used herein, the term 'neutralising antibody' describes an antibody that is capable of neutralising the biological signalling activity of IL-17, for example by blocking binding of IL-17 to the IL-17R.

In a first aspect, the present invention provides a neutralising antibody having specificity for human IL-17, comprising a heavy chain, wherein the variable domain of the heavy chain comprises at least one of a CDR having the sequence given in SEQ ID NO:5 for CDR-H1, a CDR having the sequence given in SEQ ID NO:6 for CDR-H2 and a CDR having the sequence given in SEQ ID NO:7 for CDR-H3.

Preferably, an antibody of the first aspect of the present invention comprises a heavy chain wherein at least two of CDR-H1, CDR-H2 and CDR-H3 of the variable domain of the heavy chain are selected from the following: the sequence given in SEQ ID NO:5 for CDR-H1, the sequence given in SEQ ID NO:6 for CDR-H2 and the sequence given in SEQ ID NO:7 for CDR-H3. For example, the antibody may comprise a heavy chain wherein CDR-H1 has the sequence given in SEQ ID NO:5 and CDR-H2 has the sequence given in SEQ ID NO:6. Alternatively, the antibody may comprise a heavy chain wherein CDR-H1 has the sequence given in SEQ ID NO:5 and CDR-H3 has the sequence given in SEQ ID NO:7, or the antibody may comprise a heavy chain wherein CDR-H2 has the sequence given in SEQ ID NO:6 and CDR-H3 has the sequence given in SEQ ID NO:7. For the avoidance of doubt, it is understood that all permutations are included.

More preferably, the antibody of the first aspect of the present invention comprises a heavy chain, wherein the variable domain comprises the sequence given in SEQ ID NO:5 for CDR-H1, the sequence given in SEQ ID NO:6 for CDR-H2 and the sequence given in SEQ ID NO:7 for CDR-H3.

In one embodiment, the antibody of the first aspect of the present invention comprises a heavy chain, wherein the variable domain of the heavy chain comprises the sequence given in SEQ ID NO:2.

In another embodiment, the antibody of the first aspect of the present invention comprises a heavy chain, wherein the variable domain of the heavy chain comprises a sequence having at least 60% identity or similarity to the sequence given in SEQ ID NO:2. In one embodiment, the antibody of the first aspect of the present invention comprises a heavy chain, wherein the variable domain of the heavy chain comprises a sequence having at least 90%, 95% or 98% identity or similarity to the sequence given in SEQ ID NO:2.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In a second aspect, the present invention provides a neutralising antibody having specificity for human IL-17, comprising a light chain, wherein the variable domain of the light chain comprises at least one of a CDR having the sequence given in SEQ ID NO:8 for CDR-L1, a CDR having the sequence given in SEQ ID NO:9 for CDR-L2 and a CDR having the sequence given in SEQ ID NO:10 for CDR-L3.

Preferably, the antibody of the second aspect of the present invention comprises a light chain, wherein at least two of CDR-L1, CDR-L2 and CDR-L3 of the variable domain of the light chain are selected from the following: the sequence given in SEQ ID NO:8 for CDR-L1, the sequence given in SEQ ID NO:9 for CDR-L2 and the sequence given in SEQ ID NO:10 for CDR-L3. For example, the antibody may comprise a light chain wherein CDR-L1 has the sequence given in SEQ ID NO:8 and CDR-L2 has the sequence given in SEQ ID NO:9. Alternatively, the antibody may comprise a light chain wherein CDR-L1 has the sequence given in SEQ ID NO:8 and CDR-L3 has the sequence given in SEQ ID NO:10, or the antibody may comprise a light chain wherein CDR-L2 has the sequence given in SEQ ID NO:9 and CDR-L3 has the sequence given in SEQ ID NO:10. For the avoidance of doubt, it is understood that all permutations are included.

More preferably, the antibody of the second aspect of the present invention comprises a light chain, wherein the variable domain comprises the sequence given in SEQ ID NO:8 for CDR-L1, the sequence given in SEQ ID NO:9 for CDR-L2 and the sequence given in SEQ ID NO:10 for CDR-L3.

In one embodiment, the antibody of the second aspect of the present invention comprises a light chain, wherein the variable domain of the light chain comprises the sequence given in SEQ ID NO:4.

In another embodiment, the antibody of the second aspect of the present invention comprises a light chain, wherein the variable domain of the light chain comprises a sequence having at least 60% identity or similarity to the sequence given in SEQ ID NO:4. Preferably, the antibody of the second aspect of the present invention comprises a light chain, wherein the variable domain of the light chain comprises a sequence having at least 90%, 95% or 98% identity or similarity to the sequence given in SEQ ID NO:4.

The antibody molecules of the first and second aspects of the present invention preferably comprise a complementary light chain or a complementary heavy chain, respectively.

Preferably, the antibody according to either of the first and second aspects of the present invention comprises a heavy chain, wherein the variable domain of the heavy chain comprises the sequence given in SEQ ID NO:5 for CDR-H1, the sequence given in SEQ ID NO:6 for CDR-H2 and the sequence given in SEQ ID NO:7 for CDR-H3 and a light chain wherein the variable domain of the light chain comprises the sequence given in SEQ ID NO:8 for CDR-L1, the sequence given in SEQ ID NO:9 for CDR-L2 and the sequence given in SEQ ID NO:10 for CDR-L3.

In one embodiment of the first and second aspects of the invention, the antibody comprises a heavy chain, wherein the variable domain of the heavy chain comprises the sequence given in SEQ ID NO:2 and a light chain, wherein the variable domain of the light chain comprises the sequence given in SEQ ID NO:4.

Hence in one further embodiment of the first and second aspects of the invention, the antibody comprises a heavy chain and a light chain, wherein the variable domain of the heavy chain comprises a sequence having at least 60% identity or similarity to the sequence given in SEQ ID NO:2 and the variable domain of the light chain comprises a sequence having at least 60% identity or similarity to the sequence given in SEQ ID NO:4. Preferably, the antibody comprises a heavy chain, wherein the variable domain of the light chain comprises a sequence having at least 90%, 95% or 98% identity or similarity to the sequence given in SEQ ID NO:2 and a light chain, wherein the variable domain of the light chain comprises a sequence having at least 90%, 95% or 98% identity or similarity to the sequence given in SEQ ID NO:4.

In a third aspect of the present invention, there is provided an antibody according to either the first or the second aspect of the invention, wherein said antibody is a monoclonal antibody.

In a preferred embodiment of the third aspect of the invention, the monoclonal antibody comprises a heavy chain, wherein the variable domain of the heavy chain comprises the sequence given in SEQ ID NO:2 and a light chain, wherein the variable domain of the light chain comprises the sequence given in SEQ ID NO:4.

In an alternatively preferred embodiment of the third aspect of the invention, the monoclonal antibody is a murine monoclonal antibody, wherein the monoclonal antibody comprises a heavy chain and a light chain, wherein the variable domain of the heavy chain comprises the sequence given in SEQ ID NO:2, and wherein the variable domain of the light chain comprises the sequence given in SEQ ID NO:4. This murine monoclonal antibody is referred to herein as 'IL-17F4.100' or as the "donor" antibody. The complete nucleotide and amino acid sequences of the variable domains of the heavy and light chains of mouse monoclonal antibody IL-17F4.100 are shown in FIGS. 1a and 1b and are given in SEQ ID NOS: 1 to 4. The CDRs given in SEQ ID NOS: 5 to 10 are derived from murine monoclonal antibody IL-17F4.100.

In a fourth aspect of the invention, there is provided a CDR-grafted antibody molecule, wherein one or more of the CDRs have been obtained from the murine monoclonal antibody IL-17F4.100 (SEQ ID NOS:5 to 10). As used herein, the term 'CDR-grafted antibody molecule' refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998.

When the CDRs are grafted, any appropriate acceptor variable region framework sequence may be used having regard to the class/type of the donor antibody from which the CDRs are derived, including mouse, primate and human framework regions. Preferably, the CDR-grafted antibody of the fourth aspect of the present invention has a variable domain comprising human acceptor framework regions as well as one or more of the CDRs derived from the donor antibody as referred to above. Thus, provided is a neutralising CDR-grafted antibody wherein the variable domain comprises human acceptor framework regions and non-human, preferably murine, donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.mrc-cpe.cam.ac.uk/

In a CDR-grafted antibody of the present invention, the acceptor heavy and light chains do not necessarily need to be derived from the same antibody and may, if desired, comprise composite chains having framework regions derived from different chains.

The preferred framework region for the heavy chain of the CDR-grafted antibody of the present invention is derived from the human sub-group VH3 sequence 1-3 3-33 together with JH4 (shown in FIG. 2; SEQ ID NO:20 and 21). Accordingly, provided is a neutralising CDR-grafted antibody comprising at least one non-human donor CDR wherein the heavy chain framework region is derived from the human subgroup sequence 1-3 3-33 together with JH4. The sequence of human JH4 is as follows: (YFDY)WGQGTLVTVSS (SEQ ID NO:21). The YFDY motif is part of CDR-H3 and is not part of framework 4 (Ravetch, J V. et al., 1981, Cell, 27, 583-591). The donor sequence is the IL-17F4.100 VH sequence (SEQ ID NO:2) shown in FIG. 1a.

The preferred framework region for the light chain of the CDR-grafted antibody of the present invention is derived from the human germline sub-group VK1 sequence 2-1-(1) O12 together with JK1 shown in FIG. 2 (SEQ ID NO:22 and 23). Accordingly, provided is a neutralising CDR-grafted antibody comprising at least one non-human donor CDR wherein the light chain framework region is derived from the human subgroup sequence VK1 2-1-(1) O12 together with JK1. The JK1 sequence is as follows: (WT)FGQGTKVEIK (SEQ ID NO:23). The WT motif is part of CDR-L3 and is not part of framework 4 (Hieter, P A., et al., 1982, J. Biol. Chem., 257, 1516-1522). The donor sequence is the IL-17F4.100 VL sequence (SEQ ID NO:4) shown in FIG. 1b.

Also, in a CDR-grafted antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

Preferably, in a CDR-grafted antibody molecule of the present invention, if the acceptor heavy chain has the human VH3 sequence 1-3 3-33 together with JH4, then the acceptor framework regions of the heavy chain comprise, in addition to one or more donor CDRs, a donor residue at at least one of positions 24 and 78, preferably at both position 24 and 78 (according to Kabat et al., (supra)). Accordingly, provided is a CDR-grafted antibody, wherein at least the residues at position 24 and 78 of the variable domain of the heavy chain are donor residues.

Preferably, in a CDR-grafted antibody molecule according to the present invention, if the acceptor light chain has the human sub-group VK1 sequence 2-1-(1) O12 together with JK1, then the acceptor framework regions of the light chain comprise a donor residue at position 2 (according to Kabat et al., supra). Accordingly, provided is a CDR-grafted antibody wherein at least the residue at position 2 is a donor residue.

Donor residues are residues from the donor antibody, i.e. the antibody from which the CDRs were originally derived, which in the case of the present invention is the murine monoclonal antibody IL-17F4.100.

In an alternative embodiment of the first or fourth aspects of the present invention, the heavy chain preferably comprises the sequence of gH11 (SEQ ID NO:11). The sequence of the variable domain of this grafted heavy chain is shown in FIG. 3a (starting at base 64).

In an alternative embodiment of the second or fourth aspects of the present invention, the light chain preferably comprises the sequence of gL3 (SEQ ID NO:13). The sequence of the variable domain of this grafted light chain is shown in FIG. 3b (starting at base 64).

More preferably, an antibody molecule according to the alternative embodiment of the first, second or fourth aspects of the present invention comprises a heavy chain comprising the sequence of gH11 (SEQ ID NO:11) and a light chain comprising the sequence of gL3 (SEQ ID NO:13).

In one embodiment of the fourth aspect of the invention, the antibody comprises a heavy chain and a light chain, wherein the variable domain of the heavy chain comprises a sequence having at least 60% identity or similarity to the sequence given in SEQ ID NO:11 and the variable domain of the light chain comprises a sequence having at least 60% identity or similarity to the sequence given in SEQ ID NO:13. Preferably, the antibody comprises a heavy chain, wherein the variable domain of the light chain comprises a sequence having at least 90%, 95% or 98% identity or similarity to the sequence given in SEQ ID NO:11 and a light chain, wherein the variable domain of the light chain comprises a sequence having at least 90%, 95% or 98% identity or similarity to the sequence given in SEQ ID NO:13.

The antibody molecule of the present invention may comprise a complete antibody molecule having full length heavy and light chains or a fragment thereof, such as a Fab, modified Fab, Fab', F(ab')$_2$, Fv or scFv fragment. Alternatively, it may comprise a light chain or heavy chain monomer or dimer or a single chain antibody, e.g. a single chain Fv in which the heavy and light chain variable domains are joined by a peptide linker. Similarly, the heavy and light chain variable regions may be combined with other antibody domains as appropriate. The methods for creating and manufacturing these antibody fragments are well known in the art (see for example Verma et al., 1998, Journal of Immunological Methods, 216, 165-181).

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking IL-17 activity.

Particular antibody fragments for use in the present invention include Fab and Fab' fragments and those described in International patent applications WO2005/003169, WO2005/003170 and WO2005/003171 (Published 13.1.2005). In particular the modified antibody Fab fragments described in International patent application WO2005/003169 are preferred. These Fab fragments comprise a heavy and light chain pair, $V_H/C_H1$ and $V_L/C_L$ covalently linked through interchain cysteines in the heavy and light chain constant regions and are characterised in that the heavy chain constant region terminates at the interchain cysteine of $C_H1$. The term 'interchain cysteine' refers to a cysteine in the heavy or light chain constant region that would be disulphide linked to a cysteine in the corresponding heavy or light chain constant region encoded in a naturally occurring germline antibody gene. In particular the interchain cysteines are a cysteine in the constant region of the light chain ($C_L$) and a cysteine in the first constant region of the heavy chain ($C_H1$) that are disulphide linked to each other in naturally occurring antibodies. Examples of such cysteines may typically be found at position 214 of the light chain and 233 of the heavy chain of human IgG1, 127 of the heavy chain of human IgM, IgE, IgG2, IgG3, IgG4 and 128 of the heavy chain of human IgD and IgA2B, as defined by Kabat et al., 1987, in Sequences of Proteins of Immunological Interest, US Department of Health and Human Services, NIH, USA. In murine IgG, interchain cysteines may be found at position 214 of the light chain and 235 of the heavy chain. It will be appreciated that the exact positions of these cysteines may vary from that of naturally occurring antibodies if any modifications, such as deletions, insertions and/or substitutions have been made to the antibody Fab fragment. These antibody Fab fragments may be prepared by any suitable method known in the art. For example, the antibody Fab fragment may be obtained from any whole antibody, especially a whole monoclonal antibody, using any suitable enzymatic cleavage and/or digestion techniques, for example by treatment with pepsin or papain and c-terminal proteases. Preferably these antibody Fab fragments are prepared by the use of recombinant DNA techniques involving the manipulation and re-expression of DNA encoding antibody variable and constant regions. Standard molecular biology techniques may be used to modify, add or delete further amino acids or domains as desired. Any alterations to the variable or constant regions are still encompassed by the terms 'variable' and 'constant' regions as used herein. Preferably PCR is used to introduce a stop codon immediately following the codon encoding the interchain cysteine of $C_H1$, such that translation of the $C_H1$ domain stops at the interchain cysteine. Methods for designing suitable PCR primers are well known in the art and the sequences of antibody $C_H1$ domains are readily available (Kabat et al., supra). Alternatively stop codons may be introduced using site-directed mutagenesis techniques such as those described in White (Ed.), PCR Protocols: Current Methods and Applications (1993). In one example the constant regions in these fragments are derived from IgG1 and the interchain cysteine of $C_L$ is at position 214 of the light chain and the interchain cysteine of $C_H1$ is at position 233 of the heavy chain.

In a preferred embodiment of the first, second or fourth aspects of the invention, the antibody provided by the present invention is a neutralising antibody molecule, wherein its heavy chain comprises or consists of the sequence given in SEQ ID NO:16 and the light chain comprises or consists of the sequence given in SEQ ID:18. Most preferably, the antibody provided by the present invention is a neutralising antibody molecule with an antibody format as described in International patent application WO2005/003169 wherein its heavy chain comprises or consists of the sequence given in SEQ ID NO:16, and wherein its light chain comprises or consists of the sequence given in SEQ ID NO:18.

In one embodiment of this aspect of the invention, the antibody comprises a heavy chain and a light chain, wherein the heavy chain comprises a sequence having at least 60% identity or similarity to the sequence given in SEQ ID NO:16 and the light chain comprises a sequence having at least 60% identity or similarity to the sequence given in SEQ ID NO:18. Preferably, the antibody comprises a heavy chain, wherein the heavy chain comprises a sequence having at least 90%, 95% or 98% identity or similarity to the sequence given in SEQ ID NO:16 and a light chain, wherein the light chain comprises a sequence having at least 90%, 95% or 98% identity or similarity to the sequence given in SEQ ID NO:18.

In a fifth aspect of the invention, there is provided a specific region or epitope of human IL-17 wherein binding of IL-17F4.100 or antibodies comprising the heavy chain sequence gH11 (SEQ ID NO:11) and the light chain sequence gL3 (SEQ ID NO:13) completely neutralises the activity of the IL-17 protein.

This specific region or epitope of the human IL-17 polypeptide can be identified by any suitable epitope mapping method known in the art in combination with any one of the antibodies provided by the present invention. Examples of such methods include screening peptides of varying lengths derived from IL-17 for binding to the antibody of the present invention with the smallest fragment that can specifically bind to the antibody containing the sequence of the epitope recognised by the antibody. The IL-17 peptides may be produced synthetically or by proteolytic digestion of the IL-17 polypeptide. Peptides that bind the antibody can be identified by, for example, mass spectrometric analysis. In another example, NMR spectroscopy can be used to identify the epitope bound by an antibody of the present invention. Once identified, the epitopic fragment which binds an antibody of the present invention can be used, if required, as an immunogen to obtain additional neutralising antibodies which bind the same epitope.

Antibodies which cross-block the binding of the antibodies of the first to fourth aspects of the present invention to IL-17 may be similarly useful in neutralising IL-17 activity. In a sixth aspect of the invention, therefore, there is provided a neutralising antibody having specificity for human IL-17, which cross-blocks the binding of any one of the antibodies provided in the first to fourth aspects of the present invention to human IL-17 and/or is cross-blocked from binding IL-17 by any one of those antibodies. In one embodiment the neutralising antibody of the sixth aspect of the present invention binds to the same epitope as an antibody provided by the first to fourth aspects of the present invention. In further embodiments the neutralising antibody of the sixth aspect of the present invention binds to an epitope which borders and/or overlaps with the epitope bound by an antibody of the first to fourth aspects of the invention. In a still further embodiment the neutralising antibody of the sixth aspect of the invention does not bind to the same epitope as an antibody of the first to fourth aspects of the invention or an epitope that borders and/or overlaps with said epitope.

Cross-blocking antibodies according to the sixth aspect of the present invention can be identified using any suitable method in the art, for example by using competition ELISA or BIAcore where binding of the cross blocking antibody of the sixth aspect of the invention to human IL-17 prevents the binding of an antibody provided in the first to fourth aspects of the present invention or vice versa.

In one embodiment there is provided a neutralising antibody having specificity for human IL-17, which cross-blocks the binding of IL17F.100 or an antibody whose heavy chain comprises the sequence gH11 (SEQ ID NO:11) and whose light chain comprises the sequence gL3 (SEQ ID NO:13) to human IL-17. In one embodiment the cross-blocking antibodies provided by the sixth aspect of the invention inhibit the binding of IL17F.100 or an antibody whose heavy chain comprises the sequence gH11 (SEQ ID NO:11) and whose light chain comprises the sequence gL3 (SEQ ID NO:13) by greater than 80%, preferably by greater than 85%, more preferably by greater than 90%, even more preferably by greater than 95%.

Alternatively or in addition, antibodies according to this aspect of the invention may be cross-blocked from binding to human IL-17 by any one of the antibodies of the first to fourth aspects of the present invention. Also provided therefore is a neutralising antibody molecule having specificity for human IL-17 which is cross-blocked from binding human IL-17 by the antibody IL17F.100 or an antibody whose heavy chain comprises the sequence gH11 (SEQ ID NO:11) and whose light chain comprises the sequence gL3 (SEQ ID NO:13). In one embodiment the cross-blocking antibodies provided by the sixth aspect of the invention are inhibited from binding human IL-17 by IL17F.100 or an antibody whose heavy chain comprises the sequence gH11 (SEQ ID NO:11) and whose light chain comprises the sequence gL3 (SEQ ID NO:13) by greater than 80%, preferably by greater than 85%, more preferably by greater than 90%, even more preferably by greater than 95%.

The antibody molecule of any aspect of the present invention preferably has a high binding affinity, preferably picomolar. Preferably the antibody molecule of the present invention has a binding affinity of between about 1 and 500 pM. In one embodiment the antibody molecule of the present invention has a binding affinity of between about 100 and about 400 pM. It will be appreciated that the affinity of antibodies provided by the present invention may be altered using any suitable method known in the art. The present invention therefore also relates to variants of the antibody molecules of the present invention, which have an improved affinity for IL-17. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in PCT/GB2005/002084.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Particular optional substituents which may be present on the above-mentioned synthetic polymers include one or more hydroxy, methyl or methoxy groups.

Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Particular naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 to 40000 Da and more preferably from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO98/25971). In one example the antibody molecule of the present invention is a modified Fab fragment wherein the modification is the addition to the C-terminal end of its heavy chain one or more amino acids to allow the attachment of an effector molecule. Preferably, the additional amino acids form a modified hinge region containing one or more cysteine residues to which the effector molecule may be attached. Multiple sites can be used to attach two or more PEG molecules.

Preferably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and Sun-Bio) and M-PEG-SPA (obtainable from Nektar, formerly Shearwater).

In one embodiment, the antibody is a modified Fab fragment which is PEGylated, i.e. has PEG (poly(ethyleneglycol)) covalently attached thereto, e.g. according to the method disclosed in EP 0948544 [see also "Poly(ethyleneglycol) Chemistry, Biotechnical and Biomedical Applications", 1992, J. Milton Harris (ed), Plenum Press, New York, "Poly (ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

In one embodiment, the present invention provides a neutralising antibody molecule having specificity for human IL-17, which is a modified Fab fragment having a heavy chain comprising the sequence given in SEQ ID NO:11 and a light chain comprising the sequence given in SEQ ID NO:13 and having at the C-terminal end of its heavy chain a modified hinge region containing at least one cysteine residue to which an effector molecule is attached. Preferably the effector molecule is PEG and is attached using the methods described in (WO98/25971 and WO2004072116) whereby a lysyl-maleimide group is attached to the cysteine residue at the C-terminal end of the heavy chain, and each amino group of the lysyl residue has covalently linked to it a methoxypoly(ethyleneglycol) residue having a molecular weight of about 20,000 Da. The total molecular weight of the PEG attached to the antibody is therefore approximately 40,000 Da.

In another example effector molecules may be attached to antibody fragments using the methods described in International patent applications WO2005/003169, WO2005/003170 and WO2005/003171.

In another preferred embodiment an antibody fragment for use in the present invention is a PEGylated (i.e. has PEG (poly(ethyleneglycol)) covalently attached thereto) Fab fragment as described in International Application Number WO2005/003169. This PEGylated Fab fragment is a Fab fragment in which the heavy chain terminates at the interchain cysteine of $C_H1$ and the PEG attached to the fragment, preferably PEG-maleimide, is covalently linked to the interchain cysteine of $C_L$ and the interchain cysteine of $C_H1$. Preferably the interchain cysteine of $C_L$ is at position 214 of the light chain and the interchain cysteine of $C_H1$ is at position 233 of the heavy chain. As discussed above the total amount of PEG attached to the fragment may be varied as desired. In one example each polymer attached to the Fab preferably has a molecular weight of approximately 20,000 Da. For example, the molecular weight may be 15,000-25,000 Da, or preferably 18,000-22,000 Da, and even more preferably 20,000 Da. The total molecular weight of the PEG attached to the antibody is therefore approximately 30,000 to 50,000 Da, preferably 40,000 Da.

PEG is attached to these fragments by first reducing the interchain disulphide bond between the interchain cysteines of $C_L$ and $C_H1$ and subsequently attaching the PEG to the free thiols. Once PEG is attached to the interchain cysteines there is no interchain disulphide linkage between the heavy and light chain. Suitable reducing agents for reducing the interchain disulphide bond are widely known in the art for example those described in Singh et al., 1995, Methods in Enzymology, 251, 167-73. Particular examples include thiol based reducing agents such as reduced glutathione (GSH), β-mercaptoethanol (β-ME), β-mercaptoethylamine (β-MA) and dithiothreitol (DTT). Other methods include using electrolytic methods, such as the method described in Leach et al., 1965, Div. Protein. Chem, 4, 23-27 and using photoreduction methods, such as the method described in Ellison et al., 2000, Biotechniques, 28 (2), 324-326. Preferably however, the reducing agent is a non-thiol based reducing agent, preferably one of the trialkylphosphine reducing agents (Ruegg U T and Rudinger, J., 1977, Methods in Enzymology, 47, 111-126; Burns J et al., 1991, J. Org. Chem, 56, 2648-2650; Getz et al., 1999, Analytical Biochemistry, 273, 73-80; Han and Han, 1994, Analytical Biochemistry, 220, 5-10; Seitz et al., 1999, Euro. J. Nuclear Medicine, 26, 1265-1273), particular examples of which include tris(2-carboxyethyl)phosphine (TCEP), tris butyl phosphine (TBP), tris-(2-cyanoethyl)phosphine, tris-(3-hydroxypropyl)phosphine (THP) and tris-(2-hydroxyethyl)phosphine. Most preferred are the reducing agents TCEP and THP. It will be clear to a person skilled in the art that the concentration of reducing agent can be determined empirically, for example, by varying the concentration of reducing agent and measuring the number of free thiols produced. Typically the reducing agent is used in excess over the antibody fragment for example between 2 and 1000 fold molar excess. Preferably the reducing agent is in 2, 3, 4, 5, 10, 100 or 1000 fold excess. In one embodiment the reductant is used at between 2 and 5 mM.

The reduction and PEGylation reactions may generally be performed in a solvent, for example an aqueous buffer solution such as acetate or phosphate, at around neutral pH, for example around pH 4.5 to around pH 8.5, typically pH 4.5 to 8, suitably pH6 to 7. The reactions may generally be performed at any suitable temperature, for example between about 5° C. and about 70° C., for example at room temperature. The solvent may optionally contain a chelating agent such as EDTA, EGTA, CDTA or DTPA. Preferably the solvent contains EDTA at between 1 and 5 mM, preferably 2 mM. Alternatively or in addition the solvent may be a chelating buffer such as citric acid, oxalic acid, folic acid, bicine, tricine, tris or ADA. The PEG will generally be employed in excess concentration relative to the concentration of the antibody fragment. Typically the PEG is in between 2 and 100 fold molar excess, preferably 5, 10 or 50 fold excess.

Where necessary, the desired product containing the desired number of PEG molecules may be separated from any starting materials or other product generated during the production process by conventional means, for example by chromatography techniques such as ion exchange, size exclusion, protein A, G or L affinity chromatography or hydrophobic interaction chromatography.

Hence in one preferred embodiment, the present invention provides a neutralising antibody molecule having specificity for human IL-17, which is a Fab fragment as described in International Application Number WO2005/003169, having a heavy chain comprising the sequence given in SEQ ID NO:16 and a light chain comprising the sequence given in SEQ ID NO:18 to which one or more effector molecules is attached, preferably two or more.

Figure 15:
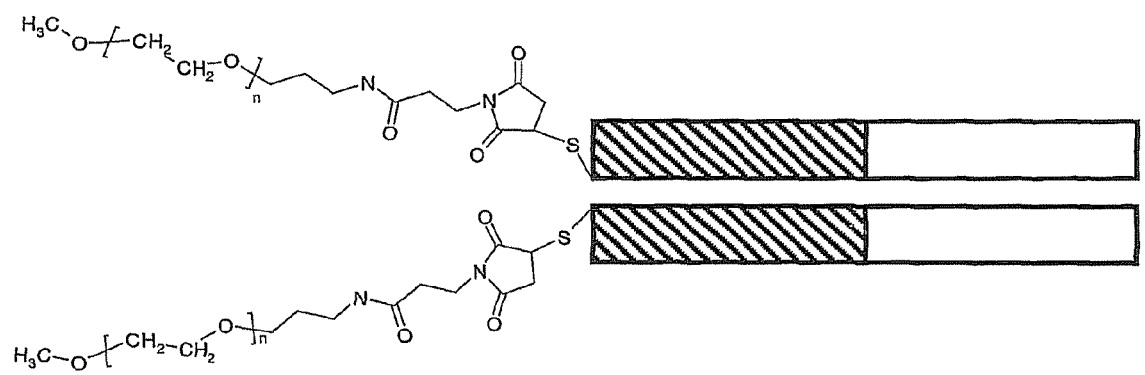

Most preferably, the antibody of the present invention is a PEGylated (i.e. has PEG (poly(ethyleneglycol)) covalently attached thereto) Fab fragment as described in International Application Number WO2005/003169. The present invention therefore provides a PEGylated Fab fragment, CDP435, which is a neutralising antibody molecule having specificity for human IL-17, having a heavy chain comprising the sequence given in SEQ ID NO:16 and a light chain comprising the sequence given in SEQ ID NO:18 to which PEG, preferably PEG-maleimide, is covalently linked to the interchain cysteine of $C_L$ and the interchain cysteine of $C_H1$. Preferably the interchain cysteine of $C_L$ is at position 214 of the light chain and the interchain cysteine of $C_H1$ is at position 233 of the heavy chain (Kabat et al. (supra)). In the antibody fragment of CDP435 these cysteines can be found by sequential numbering at positions 222 and 218 of the heavy and light chain respectively. Preferably each PEG attached to the Fab has a molecular weight of approximately 20,000 Da and the total molecular weight of the PEG attached to the Fab is therefore approximately 40,000 Da. A diagrammatic representation of the structure of the PEGylated Fab fragment, CDP435 is shown in FIG. 15. n is typically between about 400 and about 520. In one example n is between 415 and 505. In one example n is about 460.

The present invention also provides an isolated DNA sequence encoding the heavy and/or light chain(s) of an antibody molecule of the present invention. Preferably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable sequences are provided in SEQ ID NO:1; SEQ ID NO:3; SEQ ID NO:12; SEQ ID NO:14; SEQ ID NO:15 and SEQ ID NO:17.

The present invention also relates to a cloning or expression vector comprising one or more DNA sequences of the present invention. Accordingly, provided is a cloning or expression vector comprising one or more DNA sequences encoding an antibody of the present invention. Preferably, the cloning or expression vector comprises two DNA sequences, encoding the light chain and the heavy chain of the antibody molecule of the present invention, respectively. Preferably, a vector according to the present invention comprises the sequence given in SEQ ID NO:19. Bases 1-63 and 722-784 encode the *E. coli* OmpA leader sequence which is most preferably cleaved to give a neutralising antibody molecule of the present invention. Bases 718 to 721 between the light and heavy chain sequences represent an intergenic sequence for use in antibody expression in *E. coli* (WO03/048208).

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example *E. coli*, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines.

The pharmaceutical compositions preferably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, preferably 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days)

it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO 98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

It is also envisaged that the antibody of the present invention will be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides an antibody molecule for use in the control of inflammatory diseases. Preferably, the antibody molecule can be used to reduce the inflammatory process or to prevent the inflammatory process.

The present invention also provides the antibody molecule of the present invention for use in the treatment or prophylaxis of a pathological disorder that is mediated by IL-17 or associated with an increased level of IL-17. Preferably, the pathological condition is selected from the group consisting of infections (viral, bacterial, fungal and parasitic), endotoxic shock associated with infection, arthritis, rheumatoid arthritis, asthma, pelvic inflammatory disease, Alzheimer's Disease, Crohn's disease, Peyronie's Disease, coeliac disease, gallbladder disease, Pilonidal disease, peritonitis, psoriasis, vasculitis, surgical adhesions, stroke, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, gastric cancer and colon cancer), heart disease including ischaemic diseases such as myocardial infarction as well as atherosclerosis, intravascular coagulation, bone resorption, osteoporosis, periodontitis and hypochlorhydia.

The present invention also provides an antibody molecule according to the present invention for use in the treatment or prophylaxis of pain.

The present invention further provides the use of an antibody molecule according to the present invention in the manufacture of a medicament for the treatment or prophylaxis of a pathological disorder that is mediated by IL-17 or associated with an increased level of IL-17. Preferably the pathological disorder is rheumatoid arthritis or multiple sclerosis.

The present invention further provides the use of an antibody molecule according to the present invention in the manufacture of a medicament for the treatment or prophylaxis of pain.

An antibody molecule of the present invention may be utilised in any therapy where it is desired to reduce the effects of IL-17 in the human or animal body. IL-17 may be circulating in the body or may be present in an undesirably high level localised at a particular site in the body, for example a site of inflammation.

The antibody molecule of the present invention is preferably used for the control of inflammatory disease.

The present invention also provides a method of treating human or animal subjects suffering from or at risk of a disorder mediated by IL-17, the method comprising administering to the subject an effective amount of the antibody molecule of the present invention.

The antibody molecule of the present invention may also be used in diagnosis, for example in the in vivo diagnosis and imaging of disease states involving IL-17.

The present invention is further described by way of illustration only in the following examples, which refer to the accompanying Figures, in which:

FIG. 1a) shows the nucleotide and amino acid sequence (SEQ ID NOS:1 and 2, respectively) of the variable domains of the heavy chain, and FIG. 1b) shows the nucleotide and amino acid sequence (SEQ ID NOS:3 and 4, respectively) of the variable domains of the light chain of murine monoclonal antibody IL-17F4.100. In both figures positions 1-57 (nucleotide sequence numbering) are the natural mouse leader sequences associated with these variable regions.

FIG. 2 shows the graft design for the IL-17F4.100 heavy (FIG. 2a; SEQ ID NO:11) and light chain (FIG. 2b; SEQ ID NO:13) sequences. The symbol (1) highlights differences between donor:acceptor:grafted framework sequences. CDR's are single underlined. These are as defined by Kabat, except for CDR-H1 which encompasses both Kabat and Chothia definitions. Double-underlined sequences are donor residues retained in the grafts. Starred (*) residues are common in human sub-group VH3 germline sequences, but not present in this particular germline.

FIG. 3 shows the nucleotide and amino acid sequences of the designed genes gH11 (FIG. 3a) and gL3 (FIG. 3b). In both chains the E. coli OmpA leader sequence is shown (bases 1-63 of the nucleotide sequence).

FIG. 4. Shows the amino acid sequence of the antibody Fab fragment of CDP435 (a) light chain and (b) heavy chain.

FIG. 5. Shows the amino acid and nucleotide sequence of the antibody Fab fragment of CDP435. Bases 1-63 and 722-784 represent the E. coli OmpA, leader sequence.

FIG. 6. Plasmid map of pTTOD (CDP435)

Figure 7:
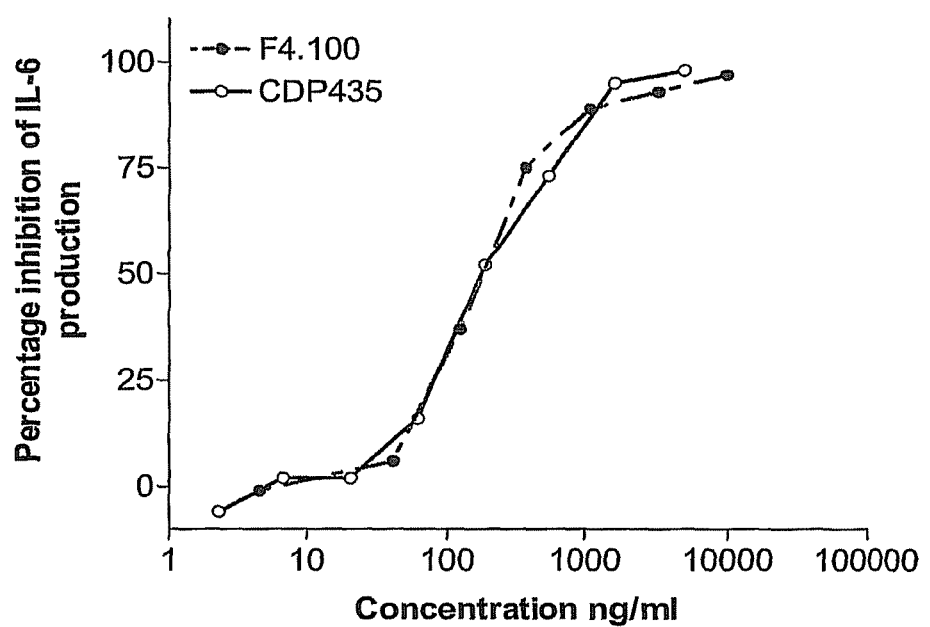

FIG. 7. A comparison of the effect of CDP435 and IL17F4.100 on human IL-17 induced IL-6 production from Hela cells.

Figure 8:
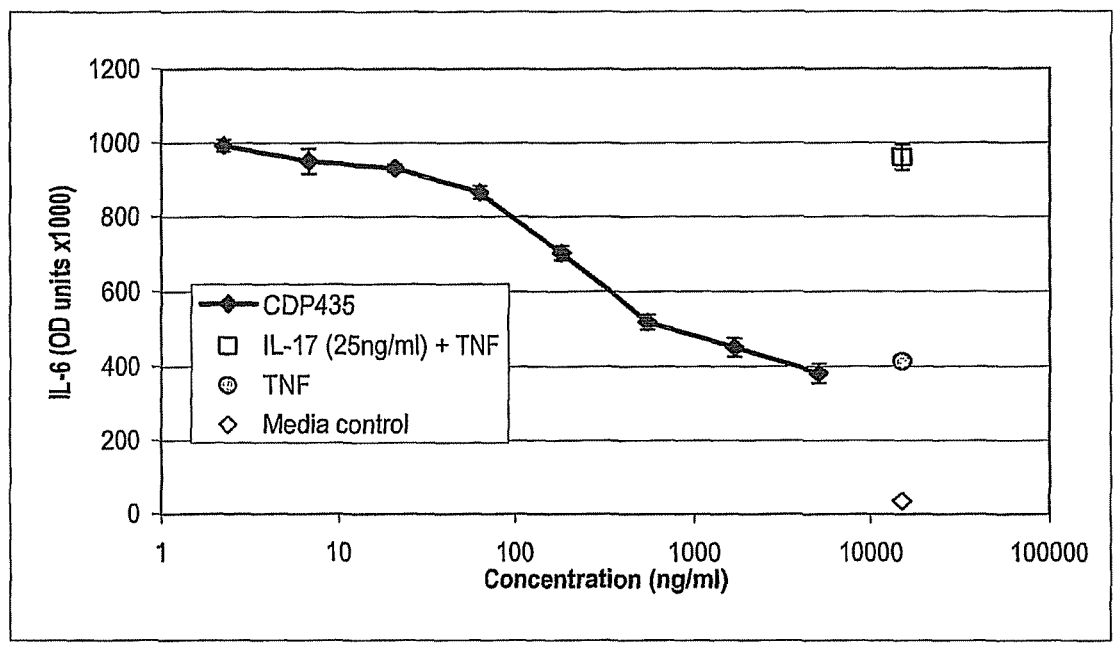

FIG. 8. The effect of CDP435 on human IL-17 induced IL-6 production from Hela cells.

Figure 9:
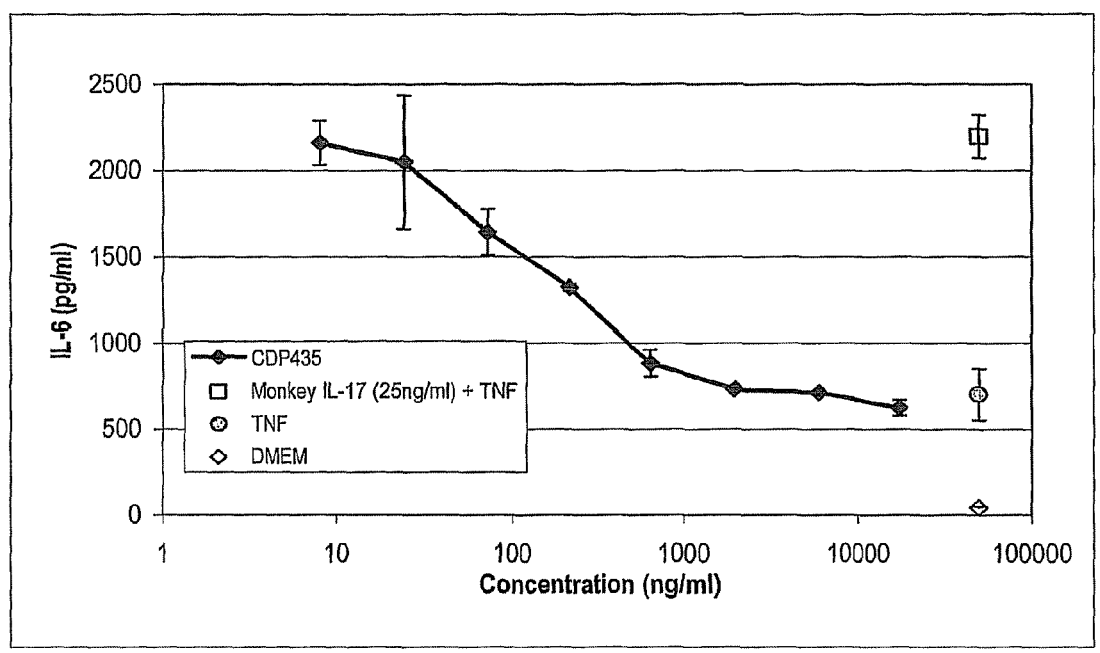

FIG. 9. The effect of CDP435 on monkey IL-17 induced IL-6 production from Hela cells.

Figure 10:
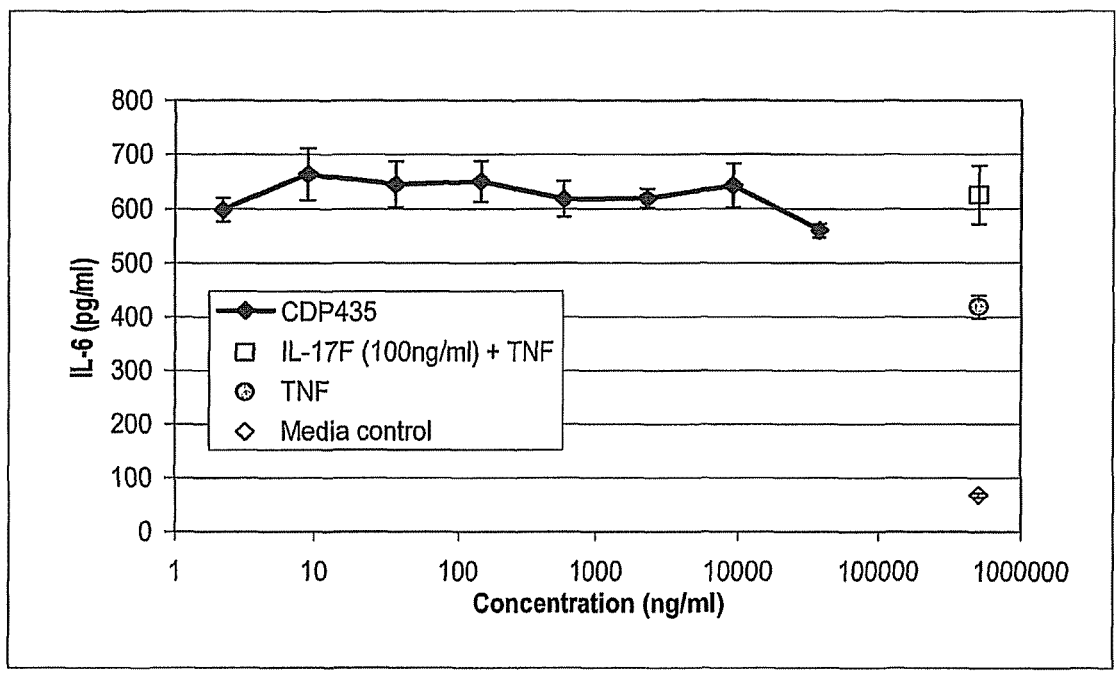

FIG. 10. The effect of CDP435 on human IL-17F induced IL-6 production from Hela cells.

Figure 11:
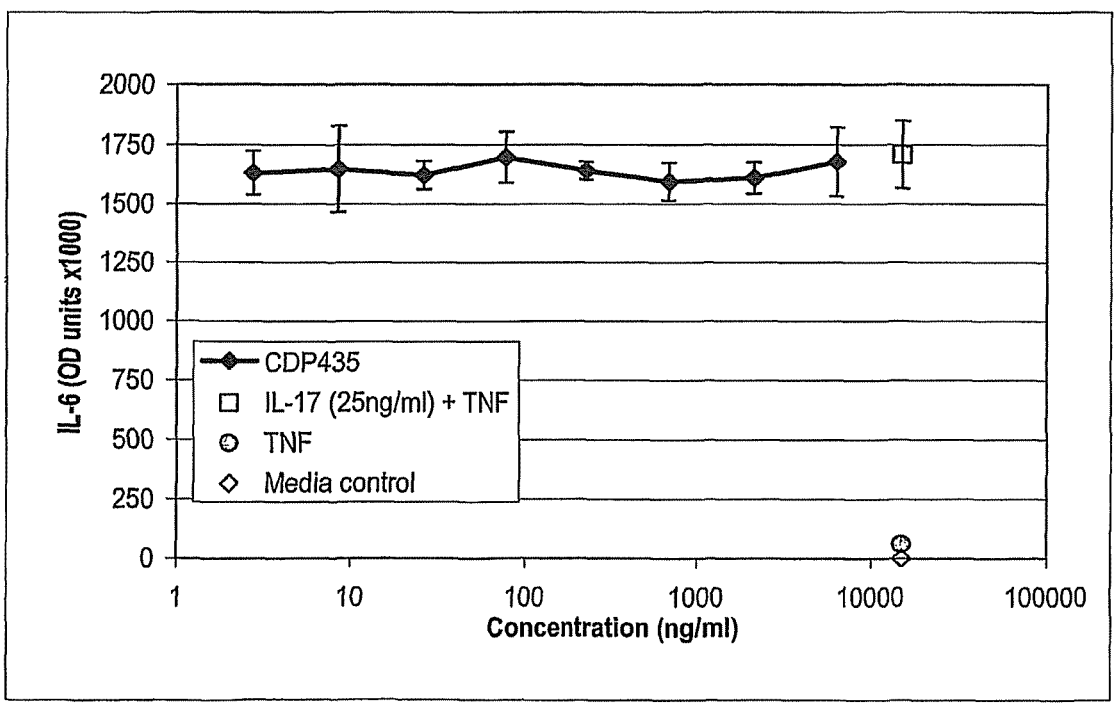

FIG. 11. The effect of CDP435 on mouse IL-17 induced IL-6 production from 3T3-NIH cells.

Figure 12:
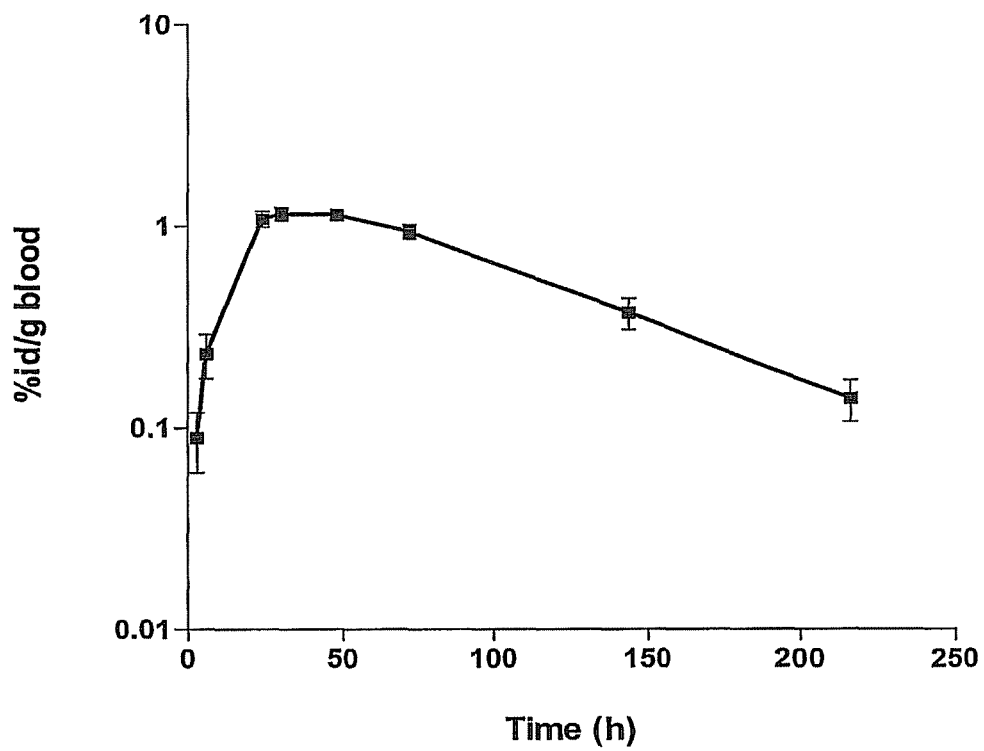

FIG. 12. Pharmacokinetics of $^{125}$I labelled CDP435 administered subcutaneously in rats FIG. 13. In vivo neutralisation of hIL-17 induced neutrophil accumulation in mice by local administration of CDP435.

Figure 14:
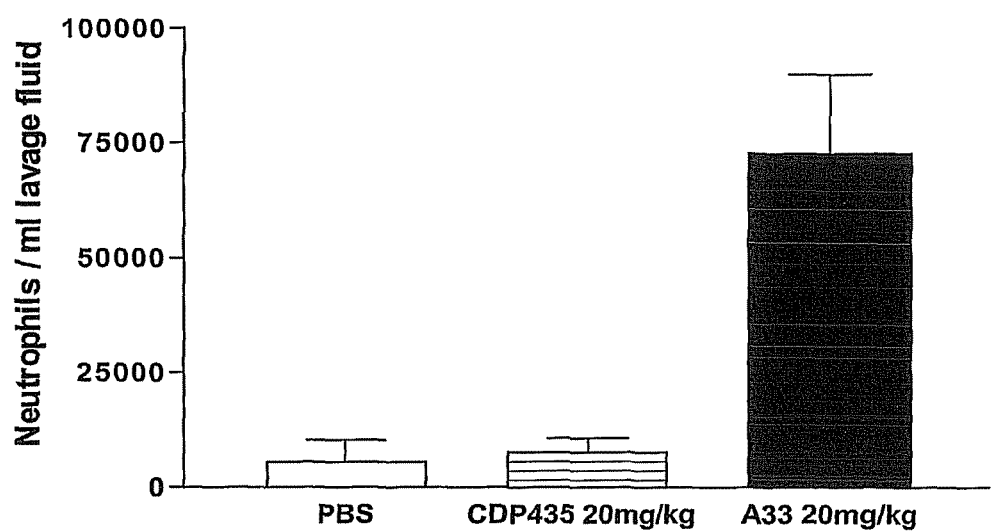

FIG. 14. In vivo neutralisation of hIL-17 induced neutrophil accumulation in mice by subcutaneous administration of CDP435.

FIG. 15. A diagrammatic representation of the structure of CDP435. n is between 400 and 520.

DNA MANIPULATIONS AND GENERAL METHODS

E. coli strain INVαF' (Invitrogen) was used for transformation and routine culture growth. DNA restriction and modification enzymes were obtained from Roche Diagnostics Ltd. and New England Biolabs. Plasmid preparations were performed using Maxi Plasmid purification kits (QIAGEN, catalogue No. 12165). DNA sequencing reactions were performed using the ABI Prism Big Dye terminator sequencing kit (catalogue No. 4304149) and run on an ABI 3100 automated sequencer (Applied Biosystems). Data was analysed using the program AutoAssembler (Applied Biosystems). Oligonucleotides were obtained from OSWEL. The concentration of Fab was determined using Fab assembly ELISA.

In Vitro Neutralisation Assay: Primary Fibroblasts

Human dermal fibroblasts were grown to 80% confluence in 96 well plates. Antibodies were titrated in half log dilutions from 1 µg/ml and human IL-17 was added to give 25 ng/ml final concentration. The plates containing antibody and human IL-17 were incubated at room temperature for 30 min. Culture medium was removed from fibroblast cultures and 100 µl antibody/IL-17 mix added to the appropriate wells and cultured overnight at 37° C. The amount of IL-8 produced in response to IL-17 was then estimated using the R&D Systems Human IL-8 Duoset Kit DY208.

EXAMPLE 1

Isolation of IL-17F4.100

Antibody IL-17F4.100 was obtained using conventional hybridoma techniques. Female BALB/C mice were immunised with recombinant human IL-17 (purchased from R & D systems). Mice received three intra peritoneal immunisations at two weekly intervals of 10 µg IL-17 in 100 µl Freund's adjuvant. Three days prior to performing the fusion the mouse was boosted with 1 µg human IL-17 in 100 µl PBS intravenously. The fusion was performed using the method of Galfre et al., 1977, Nature, 266, 550-552 with the mouse myeloma cell line SP2/0 used as the fusion partner. The fusion was screened for antibodies that bound to human IL-17 by ELISA and a number of antibody producing hybridomas were selected from this primary screen one of which was named IL-17F4.100. The hybridoma cells producing IL-17F4.100, were cloned by limiting dilution. The antibody was isotyped and found to be an IgGγ2b with a kappa light chain.

EXAMPLE 2

Gene Cloning and Expression of the Variable Regions from Murine Monoclonal Antibody IL-17F4.100

PCR Cloning of VH and VL Regions

Genes for the heavy chain variable domain (VH) and light chain variable domain (VL) of IL-17F4.100 were isolated and sequenced following cloning via reverse transcription PCR.

The V-region sequences are shown in FIG. 1 (starting at base 58) and in SEQ ID NOS:1 to 4.

The murine V-region genes were sub-cloned into expression vectors containing the human antibody constant region genes (human kappa light chain and gamma-4 heavy chain) and a mouse/human chimeric expressed transiently in CHO cells. Transfections of CHO cells were performed using the lipofectamine procedure according to manufacturer's instructions (InVitrogen, catalogue No. 18324).

EXAMPLE 3

CDR-Grafting of IL-17F4.100

A series of humanised VL and VH regions were designed in which the CDR hypervariable regions plus a varying number of framework residues from IL-17F4.100 were grafted onto human V-region acceptor frameworks.

Three grafted VL regions (gL1-3) were designed and genes were built by oligonucleotide assembly and PCR mutagenesis. A total of 16 grafted VH regions were also constructed (gH1-16). These humanised sequences were sub-cloned into vectors containing human antibody constant region genes, were expressed transiently in CHO cells and their activity in IL-17 binding and neutralisation assays was compared to the chimeric antibody comprising the IL-17F4.100 variable regions and human constant regions.

The graft most potent at neutralising IL17 was gH11gL3 which contains 1 mouse framework residue in the L chain (Val-2) and 2 mouse framework residues in the H chain (Val-24, Val-78).

FIG. 2 shows an alignment between the donor mouse sequence and the acceptor human frameworks. The heavy chain acceptor framework is the human germline sequence VH3 1-3 3.33, with framework 4 coming from this portion of the human JH-region germline JH4. The light chain acceptor framework is the human germline sequence VK1 2-1-(1) O12, with framework 4 coming from this portion of the human JK-region germline JK1. The graft sequences for gH11 and gL3 are given in FIGS. 3a (bases 64-420) and 3b (bases 64-399) respectively (SEQ ID NOS:11-14).

EXAMPLE 4

Production and Characterisation of CDP435

CDP435 is a PEGylated antibody fragment according to the present invention in which the antibody component is an antibody Fab fragment constructed from the grafts produced in Example 3. The antibody Fab fragment component of CDP435 was constructed using the genes encoding the selected humanised variable domain graft (gH11gL3) which were sub-cloned into Celltech's E. coli expression vector pTTOD, which contains DNA encoding the human Cγ1 heavy chain CH1 domain and the human C kappa light chain domain (as previously described in WO03/048208). In contrast to WO03/048208 the human heavy chain was truncated in the constant region such that the interchain disulphide cysteine (cys-233 by Kabat numbering system, cys-222 by sequential numbering) is the C-terminal residue. The protein sequence of this CDR-grafted Fab is shown in FIGS. 4a and 4b (Seq ID NOS: 15-18). A map of the pTTOD(CDP435) dicistronic expression vector is shown in FIG. 6 which comprises the construct provided in FIG. 5 and SEQ ID NO:19. The construct contains an intergenic sequence, IGS-2, between the light and heavy chain genes (See WO03/048208) and the OmpA leader sequence at the start of both the light and heavy chain genes.

The pTTOD(CDP435) vector was transformed into the host strain E. coli K12 W3110 and the antibody Fab fragment component of CDP435 produced in E. coli by high cell density cultivation using standard methods. Antibodies were purified using cation exchange followed by anion exchange chromatography using standard methods (Humphreys et al., 2002, Protein Expression and Purification, 26, 309-320).

Production of CDP435

Two 20 kDa PEG molecules were attached to the purified antibody Fab fragment component of CDP435 using the following method (See also the method provided in International patent application WO2005/003169). The purified antibody Fab fragment produced as described above was reduced to produce 2 thiols per Fab (both interchain cysteines) with 10 mM tris-(2-carboxyethyl)-phosphine (TCEP) for 1 hour at ambient temperature. The reductant was removed by diafiltration into 0.1M phosphate+2 mM EDTA, pH 6.0. The reduced antibody fragment of CDP435 was DiPEGylated on the interchain cysteines with a 3-fold molar excess of 20 kDa PEG-maleimide over Fab, overnight at ambient temperature in order to attach a total of 40 kDa PEG (i.e. 2×20 kDa PEG) to produce CDP435. A diagrammatic representation of CDP435 is shown in FIG. 15.

After PEGylation the reaction was conditioned for purification of CDP435 by reducing the pH to 4.5 (addition of acetic acid) and reducing the conductivity to 3 mS/cm (addition of water). CDP435 was purified by SP Sepharose HP chromatography in 50 mM acetate pH 4.5. Purified material was concentrated and diafiltered into 50 mM acetate, 125 mM NaCl, pH 5.5, and 0.22 μm sterile filtered.

BIAcore Assay

The assay format used CDP435 captured by anti-human IgG F(ab)$_2$ with a titration of recombinant human IL-17 in the solution phase. BIA (Biamolecular Interaction Analysis) was performed using a BIAcore 3000 (BIAcore AB). Affinipure F(ab')$_2$ Fragment goat anti-human IgG, F(ab)$_2$ fragment specific (Jackson ImmunoResearch) was immobilised on a CM5 Sensor Chip via amine coupling chemistry to a capture level of ≈9000 response units (RUs). HBS-EP buffer (10 mM HEPES pH 7.4, 0.15 M NaCl, 3 mM EDTA, 0.005% Surfactant P20, BIAcore AB) was used as the running buffer with a flow rate of 10 μl/min. An injection of CDP435 was made at 10 μl/min in order to obtain around 200 Ru of Fab captured by the immobilised anti-human IgG-F(ab)$_2$ to the surface. Human IL-17 was titrated over the captured antibody Fab fragment at various concentrations at a flow rate of 30 μl/min. The surface was regenerated by a 2×10 μl injection of 40 mM HCl, followed by a 5 μl injection of 5 mM NaOH at a flow rate of 10 μl/min.

Background subtraction binding curves were analysed using the BIAevaluation software (version 3.2) following standard procedures. Kinetic parameters were determined from the fitting algorithm. The affinity was measured at human IL-17 concentrations at or below 12.5 nM. The affinity value determined for CDP435 was in the range 133-365 pM with a mean±SD of 223.8±94.5 pM (Table 1).

TABLE 1

Affinity by BIAcore

| Replicate | $k_a$ (M$^{-1}$s$^{-1}$) | $k_d$ (s$^{-1}$) | $K_d$ (M) | $K_d$ pM |
|---|---|---|---|---|
| 1 | 1.71E+06 | 3.23E−04 | 1.891E−10 | 189 |
| 2 | 1.35E+06 | 1.79E−04 | 1.33E−10 | 133 |
| 3 | 1.83E+06 | 4.99E−04 | 2.72E−10 | 272 |
| 4 | 2.57E+06 | 4.11E−04 | 1.60E−10 | 160 |
| 5 | 1.62E+06 | 5.92E−04 | 3.65E−10 | 365 |

FIG. 7 demonstrates that the neutralisation activity of the antibody Fab fragment of CDP435 is equivalent to that of the murine parental antibody IL-17F4.100 in the Hela cell human IL-17 neuralisation assay (methods as described in Example 5).

EXAMPLE 5

In Vitro Neutralisation Assays Using CDP435

Hela Cells

The potency of CDP435 against human recombinant IL-17, monkey recombinant IL-17 and human recombinant IL-17F in Hela cells was tested. Hela cells were obtained from the cell bank at ATCC (ATCC CCL-2). Cells were grown in Dulbecco's modified Eagle's medium (DMEM) supplemented with 10% foetal calf serum, penicillin, gentamycin and glutamine. 1×10$^4$ cells were plated out into 96 well flat bottomed tissue culture plates. Cells were incubated overnight and washed once in assay buffer. Either human IL-17 (25 ng ml$^{-1}$), monkey IL-17 (25 ng ml$^{-1}$) or human IL-17F (100 ng ml$^{-1}$) was incubated in the presence of a fixed concentration of human TNF-α this mixture was preincubated with CDP435. Cytokine plus antibody was then added to the Hela cells which were incubated overnight. The production of IL-6 in the cell culture supernatant was proportionate to the amount of IL-17/IL-17F added to the cells. Human IL-6 levels were measured by ELISA and quantified by comparison with known standard concentrations of human IL-6.

The data (FIGS. 8, 9 and 10) indicates that CDP435 potently neutralised both human recombinant IL-17 and monkey recombinant IL-17 but did not inhibit the activity of human recombinant IL-17F. The data from these experiments indicated that CDP435 gave an $IC_{50}$ of 158 ng ml$^{-1}$±48 against human recombinant IL-17 (25 ng ml$^{-1}$) and 147 ng ml$^{-1}$±45 against monkey recombinant IL-17 (25 ng ml$^{-1}$).

Mouse IL-17 Neutralisation Assay (3T3-NIH Cells)

The neutralisation potency of CDP435 against mouse recombinant IL-17 was determined 3T3-NIH cells were obtained from the cell bank at ATCC (ATCC CRL-1658). Cells were grown in DMEM supplemented with 10% calf serum, penicillin, gentamycin and glutamine. The assay buffer used was identical to this buffer with foetal calf serum replacing calf serum. 1×10$^4$ cells were plated out into 96 well flat bottomed tissue culture plates. Cells were incubated overnight and washed once in assay buffer. Murine IL-17 in the presence of a fixed concentration of human TNF-α was pre-incubated with CDP435. Cytokine plus CDP435 was then added to the 3T3-NIH cells which were incubated overnight. The production of IL-6 in the cell culture supernatant was proportionate to the amount of mouse IL-17 added to the cells. Mouse IL-6 levels were measured by ELISA and quantified by comparison with known standard concentrations of murine IL-6.

The data indicates that CDP435 did not inhibit the activity of mouse recombinant IL-17 (FIG. 11).

EXAMPLE 6

Rat Pharmacokinetic Study with CDP435

Rats were injected s.c. with $^{125}$I labelled CDP435. At various times the animals were bled and the blood counted for radioactivity. The pharmacokinetic trace is shown in FIG. 12.

$AUC_{0-\infty}$=2651% dose*h, $t\frac{1}{2}\beta$=52 h, $C_{max}$=22.7% dose. The results showed that CDP435 had good pharmacokinetics with a half life of 52 hours.

CDP435 was labelled with $^{125}$I at a specific activity of 0.07 μCi/μg and 77.6 μg antibody administered s.c. in a volume of 100 μl.

In Vivo Neutralisation Assay

To determine the neutralisation efficacy of CDP435 in vivo, CDP485 was tested in two in vivo models of inflammation.

Intraperitoneal CDP435/Intraperitoneal hIL-17 in Mice

Figure 13:
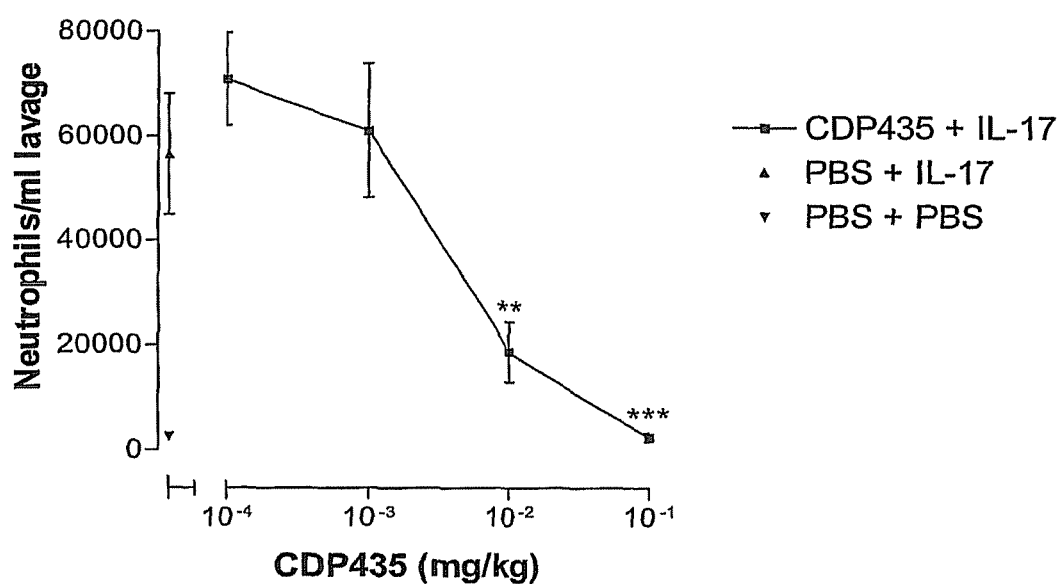

Male Balb/c mice (18-25 g) were injected intraperitoneally (i.p.) with CDP435 or control Fab' A33-PEG and then injected i.p. 5 minutes later with hIL-17. After 180 minutes, mice were killed by cervical dislocation and peritoneal lavage performed (3 ml HBSS (Hanks' Balanced Salts)+0.25% BSA, 12 mM HEPES) and neutrophil accumulation quantified by FACS (Neutrophils were identified as those cells expressing CD45 and high levels of GR1 by staining with anti-CD45 CyChrome and anti-GR1 Phycoerythrin antibodies). Neutrophil accumulation in response to 300 ng hIL-17 was significantly reduced with CDP435 at doses of 0.01 and 0.1 mg/kg (FIG. 13).

In a separate experiment animals were dosed s.c. with 20 mg/kg CDP435 and challenged i.p. with 300 ng hIL-17 24 hours later. After a further 3 hours, peritoneal lavage showed that the CDP435 treatment had blocked neutrophil accumulation (FIG. 14). Thus CDP435 is effective against hIL-17 when given locally with the antigen or administered s.c. at a distant site.

It will of course be understood that the present invention has been described by way of example only, is in no way meant to be limiting, and that modifications of detail can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication were specifically and individually indicated to be incorporated by reference herein as though fully set forth.

The invention claimed is:

1. A neutralising antibody having specificity for human IL-17, wherein the antibody binds the same epitope as an antibody comprising a light chain and a heavy chain, wherein the variable domain of the heavy chain comprises SEQ ID NO:5 for CDR-H1, SEQ ID NO:6 for CDR-H2, and SEQ ID NO:7 for CDR-H3 and wherein the variable domain of the light chain comprises SEQ ID NO:8 for CDRL1, SEQ ID NO:9 for CDR-L2, and SEQ ID NO:10 for CDR-L3.

2. The neutralising antibody having specificity for human IL-17 according to claim 1, wherein the antibody cross-blocks the binding of an antibody in which the variable domain of the heavy chain comprises the sequence gH11 (SEQ ID NO: 11) and the variable domain of the light chain comprises the sequence gL3 (SEQ ID NO: 13) to human IL-17.

3. The neutralising antibody having specificity for human IL-17 according to claim 1, wherein the antibody cross-blocks the binding of an antibody in which the variable domain of the heavy chain comprises SEQ ID NO:5 for CDR-H1, SEQ ID NO:6 for CDR-H2, and SEQ ID NO:7 for CDR-H3 and wherein the variable domain of the light chain comprises SEQ ID NO:8 for CDRL1, SEQ ID NO:9 for CDR-L2, and SEQ ID NO:10 for CDR-L3 to human IL-17.

4. The neutralising antibody having specificity for human IL-17, according to any one of claims 1, 2 and 3, wherein the antibody affinity for human IL-17 is between 100 pM and 400 pM.

5. The neutralising antibody having specificity for human IL-17, according to any one of claims 1, 2 and 3, wherein the antibody affinity for human IL-17 is less than 500 pM.

6. The neutralising antibody having specificity for human IL-17 according to claim 1, wherein one or more effector molecules are attached to said antibody.

7. A pharmaceutical composition comprising the antibody according to claim 1.

* * * * *

SEQUENCE LISTING

```
<160> NUMBER OF SEQ ID NOS: 23

<210> SEQ ID NO 1
<211> LENGTH: 357
<212> TYPE: DNA
<213> ORGANISM: Mus musculus

<400> SEQUENCE: 1
caggtgcagc tgaaggagtc aggacctggc ctggtggcgc cctcacagag cctgtccatc      60
acatgcaccg tctcagggtt ctcattaact acctatggt tacactggat tcgccagcct     120
ccaggaaagg gtctggagtg gctggtagtg atttggagtg atggatacac aacctataat     180
tcagctctca aatccagact gagcatcacc aaggacaact ccaagagcca agttttctta     240
aaaatgaaca gtctccaaac tgatgacaca gccatgtact actgtgccag aaatgatggt     300
gactacttct attctatgga ctactggggt caaggaacct cagtcaccgt ctcctca       357

<210> SEQ ID NO 2
<211> LENGTH: 119
<212> TYPE: PRT
<213> ORGANISM: Mus musculus
```

<400> SEQUENCE: 2

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Tyr
            20                  25                  30

Gly Val His Trp Ile Arg Gln Pro Pro Gly Lys Gly Leu Glu Trp Leu
        35                  40                  45

Val Val Ile Trp Ser Asp Gly Tyr Thr Thr Tyr Asn Ser Ala Leu Lys
    50                  55                  60

Ser Arg Leu Ser Ile Thr Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Asn Asp Gly Asp Tyr Phe Tyr Ser Met Asp Tyr Trp Gly Gln Gly
            100                 105                 110

Thr Ser Val Thr Val Ser Ser
        115

<210> SEQ ID NO 3
<211> LENGTH: 339
<212> TYPE: DNA
<213> ORGANISM: Mus musculus

<400> SEQUENCE: 3
gatgttgtga tgacccaaac tccactctcc ctgcctgtca gtcttggaga tcaagcctcc      60
ttctcttgca gatctagtca gagccttgta cacagtaatg aaacacccta tttacattgg    120
tacctgcaga agccaggcca gtctccaaag ctcctgatct acaaagtttc caaccgattt    180
tctggggtcc cagacaggtt cagtggcagt gggtcaggga cagatttcac actcaagatc    240
agcagagtgg aggctgagga tctgggagtt tatttctgct ctcaaagtac acatgttccg    300
acgttcggtg gaggcaccaa gctggaaatc aaacgtacg                            339

<210> SEQ ID NO 4
<211> LENGTH: 112
<212> TYPE: PRT
<213> ORGANISM: Mus musculus

<400> SEQUENCE: 4

Asp Val Val Met Thr Gln Thr Pro Leu Ser Leu Pro Val Ser Leu Gly
1               5                   10                  15

Asp Gln Ala Ser Phe Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Thr Phe Gly Gly Gly Thr Lys Leu Glu Ile Lys Arg
            100                 105                 110

<210> SEQ ID NO 5
<211> LENGTH: 10
<212> TYPE: PRT

```
<213> ORGANISM: Mus musculus

<400> SEQUENCE: 5

Gly Phe Ser Leu Thr Thr Tyr Gly Val His
1               5                   10

<210> SEQ ID NO 6
<211> LENGTH: 16
<212> TYPE: PRT
<213> ORGANISM: Mus musculus

<400> SEQUENCE: 6

Val Ile Trp Ser Asp Gly Tyr Thr Thr Tyr Asn Ser Ala Leu Lys Ser
1               5                   10                  15

<210> SEQ ID NO 7
<211> LENGTH: 11
<212> TYPE: PRT
<213> ORGANISM: Mus musculus

<400> SEQUENCE: 7

Asn Asp Gly Asp Tyr Phe Tyr Ser Met Asp Tyr
1               5                   10

<210> SEQ ID NO 8
<211> LENGTH: 16
<212> TYPE: PRT
<213> ORGANISM: Mus musculus

<400> SEQUENCE: 8

Arg Ser Ser Gln Ser Leu Val His Ser Asn Gly Asn Thr Tyr Leu His
1               5                   10                  15

<210> SEQ ID NO 9
<211> LENGTH: 7
<212> TYPE: PRT
<213> ORGANISM: Mus musculus

<400> SEQUENCE: 9

Lys Val Ser Asn Arg Phe Ser
1               5

<210> SEQ ID NO 10
<211> LENGTH: 8
<212> TYPE: PRT
<213> ORGANISM: Mus musculus

<400> SEQUENCE: 10

Ser Gln Ser Thr His Val Pro Thr
1               5

<210> SEQ ID NO 11
<211> LENGTH: 119
<212> TYPE: PRT
<213> ORGANISM: Artificial
<220> FEATURE:
<223> OTHER INFORMATION: gH11

<400> SEQUENCE: 11

Glu Val Gln Leu Val Glu Ser Gly Gly Gly Val Val Gln Pro Gly Gly
1               5                   10                  15

Ser Leu Arg Leu Ser Cys Ala Val Ser Gly Phe Ser Leu Thr Thr Tyr
            20                  25                  30

Gly Val His Trp Val Arg Gln Ala Pro Gly Lys Gly Leu Glu Trp Val
```

```
            35                  40                  45
Ala Val Ile Trp Ser Asp Gly Tyr Thr Thr Tyr Asn Ser Ala Leu Lys
 50                  55                  60

Ser Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Asn Asp Gly Asp Tyr Phe Tyr Ser Met Asp Tyr Trp Gly Gln Gly
            100                 105                 110

Thr Leu Val Thr Val Ser Ser
            115
```

<210> SEQ ID NO 12
<211> LENGTH: 357
<212> TYPE: DNA
<213> ORGANISM: Artificial
<220> FEATURE:
<223> OTHER INFORMATION: gH11

<400> SEQUENCE: 12

```
gaggttcagc tggtcgagtc tggaggcggg gttgtccagc ctggagggag cctgcgtctc     60
tcttgtgcag ttagcggctt ctcattaact acctatggtg tacactgggt gcggcaggca    120
cctgggaagg gcctggagtg ggtggccgtg atttggagtg atggatacac aacctataat    180
tcagctctca atcccgtttt caccatttcc cgcgacaatt ctaagaacac cgtttacctc    240
cagatgaact ctctccgcgc agaggacaca gcagtctatt actgtgcacg gaatgatggt    300
gactacttct attctatgga ctactgggga caggggaccc ttgtgacagt ctcgagt      357
```

<210> SEQ ID NO 13
<211> LENGTH: 112
<212> TYPE: PRT
<213> ORGANISM: Artificial
<220> FEATURE:
<223> OTHER INFORMATION: gL3

<400> SEQUENCE: 13

```
Asp Val Gln Met Thr Gln Ser Pro Ser Ser Leu Ser Ala Ser Val Gly
  1               5                  10                  15

Asp Arg Val Thr Ile Thr Cys Arg Ser Ser Gln Ser Leu Val His Ser
             20                  25                  30

Asn Gly Asn Thr Tyr Leu His Trp Tyr Gln Gln Lys Pro Gly Lys Ala
         35                  40                  45

Pro Lys Leu Leu Ile Tyr Lys Val Ser Asn Arg Phe Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Ser Gln Ser
                 85                  90                  95

Thr His Val Pro Thr Phe Gly Gln Gly Thr Lys Val Glu Ile Lys Arg
            100                 105                 110
```

<210> SEQ ID NO 14
<211> LENGTH: 336
<212> TYPE: DNA
<213> ORGANISM: Artificial
<220> FEATURE:
<223> OTHER INFORMATION: gL3

<400> SEQUENCE: 14

```
gatgtgcaga tgacccagag tccaagcagt ctctccgcca gcgtaggcga tcgtgtgact      60
attacctgta gatctagtca gagccttgta cacagtaatg gaaacaccta tttacattgg     120
tatcagcaaa aaccgggcaa agccccgaag ctgctcatct ataaagtttc caaccgattt     180
tctggtgtgc catctcgttt cagtggcagt ggcagcggta ccgactttac cctcacaatt     240
tcgtctctcc agccggaaga tttcgccact tactattgtt ctcaaagtac acatgttccg     300
acgttcggtc agggcactaa agtagaaatc aaacgt                               336
```

```
<210> SEQ ID NO 15
<211> LENGTH: 672
<212> TYPE: DNA
<213> ORGANISM: Artificial
<220> FEATURE:
<223> OTHER INFORMATION: CDP435 Heavy chain

<400> SEQUENCE: 15
gaggttcagc tggtcgagtc tggaggcggg gttgtccagc ctggagggag cctgcgtctc      60
tcttgtgcag ttagcggctt ctcattaact acctatggtg tacactgggt gcggcaggca     120
cctgggaagg gcctggagtg ggtggccgtg atttggagtg atggatacac aacctataat     180
tcagctctca aatcccgttt caccatttcc cgcgacaatt ctaagaacac cgtttacctc     240
cagatgaact ctctccgcgc agaggacaca gcagtctatt actgtgcacg gaatgatggt     300
gactacttct attctatgga ctactgggga caggggaccc ttgtgacagt ctcgagtgct     360
tctacaaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtcg acaagaaagt tgagcccaaa     660
tcttgttaat ga                                                         672
```

```
<210> SEQ ID NO 16
<211> LENGTH: 222
<212> TYPE: PRT
<213> ORGANISM: Artificial
<220> FEATURE:
<223> OTHER INFORMATION: CDP435 Heavy chain

<400> SEQUENCE: 16

Glu Val Gln Leu Val Glu Ser Gly Gly Gly Val Val Gln Pro Gly Gly
1               5                   10                  15

Ser Leu Arg Leu Ser Cys Ala Val Ser Gly Phe Ser Leu Thr Thr Tyr
            20                  25                  30

Gly Val His Trp Val Arg Gln Ala Pro Gly Lys Gly Leu Glu Trp Val
        35                  40                  45

Ala Val Ile Trp Ser Asp Gly Tyr Thr Thr Tyr Asn Ser Ala Leu Lys
    50                  55                  60

Ser Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asn Asp Gly Asp Tyr Phe Tyr Ser Met Asp Tyr Trp Gly Gln Gly
            100                 105                 110

Thr Leu Val Thr Val Ser Ser Ala Ser Thr Lys Gly Pro Ser Val Phe
```

```
            115                 120                 125
Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys
210                 215                 220

<210> SEQ ID NO 17
<211> LENGTH: 657
<212> TYPE: DNA
<213> ORGANISM: Artificial
<220> FEATURE:
<223> OTHER INFORMATION: CDP435 Light chain

<400> SEQUENCE: 17
gatgtgcaga tgacccagag tccaagcagt ctctccgcca gcgtaggcga tcgtgtgact      60
attacctgta gatctagtca gagccttgta cacagtaatg gaaacaccta tttacattgg    120
tatcagcaaa aaccgggcaa agccccgaag ctgctcatct ataaagtttc caaccgattt    180
tctggtgtgc catctcgttt cagtggcagt ggcagcggta ccgactttac cctcacaatt    240
tcgtctctcc agccggaaga tttcgccact tactattgtt ctcaaagtac acatgttccg    300
acgttcggtc agggcactaa agtagaaatc aaacgtacgg tagcggcccc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc    600 acccatcagg gcctgagctc accagtaaca aaaagttta atagagggga gtgttaa        657

<210> SEQ ID NO 18
<211> LENGTH: 218
<212> TYPE: PRT
<213> ORGANISM: Artificial
<220> FEATURE:
<223> OTHER INFORMATION: CDP435 light chain

<400> SEQUENCE: 18

Asp Val Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95
```

Thr His Val Pro Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 19
<211> LENGTH: 1516
<212> TYPE: DNA
<213> ORGANISM: Artificial
<220> FEATURE:
<223> OTHER INFORMATION: CDP435 Heavy and Light chain in pTTOD

<400> SEQUENCE: 19
atgaaaaaga cagctatcgc aattgcagtg gccttggctg gtttcgctac cgtagcgcaa      60
gctgatgtgc agatgaccca gagtccaagc agtctctccg ccagcgtagg cgatcgtgtg     120
actattacct gtagatctag tcagagcctt gtacacagta atggaaacac ctatttacat     180
tggtatcagc aaaaaccggg caaagccccg aagctgctca tctataaagt ttccaaccga     240
ttttctggtg tgccatctcg tttcagtggc agtggcagcg gtaccgactt taccctcaca     300
atttcgtctc tccagccgga agatttcgcc acttactatt gttctcaaag tacacatgtt     360
ccgacgttcg gtcagggcac taaagtagaa atcaaacgta cggtagcggc cccatctgtc     420
ttcatcttcc cgccatctga tgagcagttg aaatctggaa ctgcctctgt tgtgtgcctg     480
ctgaataact ctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcaccagta caaaaagtt taatagagg ggagtgttaa     720 aatgaagaag actgctatag caattgcagt ggcgctagct ggtttcgcca ccgtggcgca     780
agctgaggtt cagctggtcg agtctggagg cggggttgtc cagcctggag ggagcctgcg     840
tctctcttgt gcagttagcg gcttctcatt aactacctat ggtgtacact gggtgcggca     900
ggcacctggg aagggcctgg agtgggtggc cgtgatttgg agtgatggat acacaaccta     960
taattcagct ctcaaatccc gtttcaccat ttcccgcgac aattctaaga acaccgttta    1020
cctccagatg aactctctcc gcgcagagga cacagcagtc tattactgtg cacggaatga    1080
tgaggtctac ttgagagagg cgcgtctcct gtgtcgtcag ataatgacac gtgccttact    1140

```
aggtgactac ttctattcta tggactactg gggacagggg acccttgtga cagtctcgag   1200
tgcttctaca aagggcccat cggtcttccc cctggcaccc tcctccaaga gcacctctgg   1260
gggcacagcg ccctgggct gcctggtcaa ggactacttc cccgaaccgg tgacggtgtc    1320
gtggaactca ggcgccctga ccagcggcgt gcacaccttc ccggctgtcc tacagtcctc   1380
aggactctac tccctcagca gcgtggtgac cgtgccctcc agcagcttgg gcacccagac   1440
ctacatctgc aacgtgaatc acaagcccag caacaccaag gtcgacaaga aagttgagcc   1500
caaatcttgt taatga                                                   1516
```

```
<210> SEQ ID NO 20
<211> LENGTH: 98
<212> TYPE: PRT
<213> ORGANISM: Homo sapiens

<400> SEQUENCE: 20
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

```
<210> SEQ ID NO 21
<211> LENGTH: 15
<212> TYPE: PRT
<213> ORGANISM: Homo sapiens

<400> SEQUENCE: 21
```

Tyr Phe Asp Tyr Trp Gly Gln Gly Thr Leu Val Thr Val Ser Ser
1               5                   10                  15

```
<210> SEQ ID NO 22
<211> LENGTH: 95
<212> TYPE: PRT
<213> ORGANISM: Homo sapiens

<400> SEQUENCE: 22
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

```
<210> SEQ ID NO 23
<211> LENGTH: 12
<212> TYPE: PRT
<213> ORGANISM: Homo sapiens

<400> SEQUENCE: 23

Trp Thr Phe Gly Gln Gly Thr Lys Val Glu Ile Lys
1               5                   10
```